United States Patent
Sano et al.

(10) Patent No.: US 10,478,114 B2
(45) Date of Patent: Nov. 19, 2019

(54) BRAIN DYSFUNCTION ASSESSMENT METHOD, BRAIN DYSFUNCTION ASSESSMENT DEVICE, AND PROGRAM THEREOF

(71) Applicant: MAXELL, LTD., Kyoto (JP)

(72) Inventors: Yuko Sano, Tokyo (JP); Akihiko Kandori, Tokyo (JP); Kanako Esaki, Tokyo (JP); Kazuhiro Kaizaki, Yokohama (JP); Shinya Katsuki, Yokohama (JP); Kenji Katsumata, Yokohama (JP); Tomohiko Mizuguchi, Yokohama (JP); Yasushi Saito, Yokohama (JP); Tamotsu Nagabayashi, Yokohama (JP); Tomochika Yamashita, Yokohama (JP); Takumi Okamura, Yokohama (JP)

(73) Assignee: MAXELL, LTD., Kyoto (JP)

( * ) Notice: Subject to any disclaimer, the term of this patent is extended or adjusted under 35 U.S.C. 154(b) by 410 days.

(21) Appl. No.: 14/893,338

(22) PCT Filed: Sep. 11, 2013

(86) PCT No.: PCT/JP2013/074582
§ 371 (c)(1),
(2) Date: Nov. 23, 2015

(87) PCT Pub. No.: WO2015/037089
PCT Pub. Date: Mar. 19, 2015

(65) Prior Publication Data
US 2016/0100788 A1  Apr. 14, 2016

(51) Int. Cl.
*A61B 5/00* (2006.01)
*A61B 5/11* (2006.01)
*A61B 5/12* (2006.01)

(52) U.S. Cl.
CPC .......... *A61B 5/4064* (2013.01); *A61B 5/1124* (2013.01); *A61B 5/121* (2013.01);
(Continued)

(58) Field of Classification Search
CPC ..... A61B 5/4064; A61B 5/1124; A61B 5/121; A61B 5/4088; A61B 5/4094; A61B 5/6898; A61B 5/7475
(Continued)

(56) References Cited

U.S. PATENT DOCUMENTS 6,413,190 B1 * 7/2002 Wood .................. A61B 5/1071
463/36
6,875,181 B2 * 4/2005 Kajimoto ............... A61B 5/162
128/898
(Continued)

FOREIGN PATENT DOCUMENTS

JP  06-327659 A  11/1994
JP  11-188020 A  7/1999
(Continued)

OTHER PUBLICATIONS

Robbins, T.W., et al., "Cambridge Neuropsychological Test Automated Battery (CANTAB): A factor analytic study of a large sample of normal elderly volunteers," Dementia (Basel, Switzerland), Sep. 1994, pp. 266-281.
(Continued)

*Primary Examiner* — Daniel L Cerioni
(74) *Attorney, Agent, or Firm* — Volpe and Koenig, P.C.

(57) ABSTRACT

A brain dysfunction assessment device (100) comprises: a body movement indicator (10) which presents a body movement to be performed to a subject with a body movement presentation device (2); a body movement data acquisition unit (20) which acquires the subject's body movement data with a body movement detection sensor (3); a body move-
(Continued)

ment accuracy calculation unit (30) which calculates a positional accuracy and a time sequence accuracy of the subject's body movement from the acquired body movement data; and a cognitive dysfunction assessment unit (40) which assesses the level of cognitive dysfunction of the subject by comparing a value which indicates the accuracy of the subject's body movement that is obtained from the calculated positional accuracy and time sequence accuracy with statistical data which indicates the accuracy of body movement of healthy individuals.

20 Claims, 15 Drawing Sheets

(52) U.S. Cl.
CPC .......... *A61B 5/4088* (2013.01); *A61B 5/4094* (2013.01); *A61B 5/6898* (2013.01); *A61B 5/7475* (2013.01); *A61B 5/7278* (2013.01); *A61B 5/742* (2013.01); *A61B 5/7405* (2013.01); *A61B 2560/0223* (2013.01)

(58) Field of Classification Search
USPC .......................................................... 600/595
See application file for complete search history.

(56) References Cited

U.S. PATENT DOCUMENTS

| | | | |
|---|---|---|---|
| 2002/0192624 A1* | 12/2002 | Darby | A61B 5/16 434/236 |
| 2010/0292545 A1* | 11/2010 | Berka | A61B 5/048 600/301 |
| 2010/0298649 A1* | 11/2010 | Warkentin | A61B 5/02755 600/300 |
| 2011/0018821 A1* | 1/2011 | Kii | G06F 1/1616 345/173 |
| 2011/0054361 A1 | 3/2011 | Sakoda et al. | |
| 2011/0066068 A1* | 3/2011 | Duffy | A61B 5/16 600/558 |
| 2013/0120282 A1* | 5/2013 | Kukulski | G06F 3/04883 345/173 |
| 2013/0290002 A1* | 10/2013 | Togawa | H04M 1/6025 704/275 |
| 2014/0107494 A1* | 4/2014 | Kato | A61B 5/7267 600/473 |
| 2014/0257143 A1* | 9/2014 | Friedman | A61B 5/1126 600/595 |
| 2015/0320350 A1* | 11/2015 | Ishikawa | A61B 5/4064 600/558 |

FOREIGN PATENT DOCUMENTS

| | | |
|---|---|---|
| JP | 2002-369818 A | 12/2002 |
| JP | 2005-508211 A | 3/2005 |
| JP | 2006-320424 A | 11/2006 |
| JP | 2011-045520 A | 3/2011 |
| JP | 2011-083403 A | 4/2011 |
| JP | 2012-217797 A | 11/2012 |

OTHER PUBLICATIONS

Chinese Office Action for Application No. 201380077561.5 dated May 26, 2017.

* cited by examiner

SUBJECT REGISTRATION INFORMATION DISPLAY SCREEN

| SUBJECT ID | P1234567 (ENTER ALPHANUMERIC CHARACTER) |
|---|---|
| SUBJECT NAME | YAMAUMI TARO (ENTER TEXT) |
| GENDER | MALE (SELECT MALE/FEMALE) |
| AGE | 71 (ENTER NUMBER) |
| REMARKS | abcd (ENTER DESCRIPTION) |

BODY MOVEMENT TASK SELECTION SCREEN

| SELECTION INSTRUCTION | TASK NAME | PARAMETER | SETTING VALUE |
|---|---|---|---|
| | (COMMON TO TASKS) | TIMEOUT TIME [SECOND] | 10 |
| ✓ | REACHING | PRESENTING TIME INTERVAL [SECOND] | 5 |
| | | DIFFICULTY LEVEL | 2 |
| | RHYTHM TOUCH | ... | ... |
| | | DIFFICULTY LEVEL | 2 |
| | FINGER OPENING AND CLOSING TAP | ... | ... |
| | | DIFFICULTY LEVEL | 2 |

121

FIG. 8
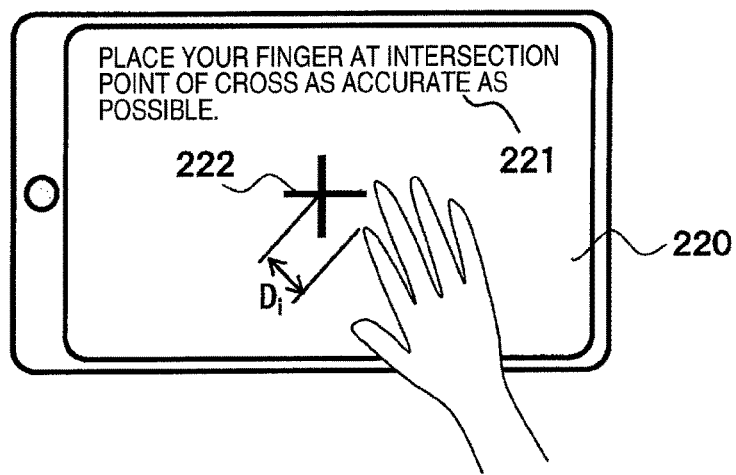
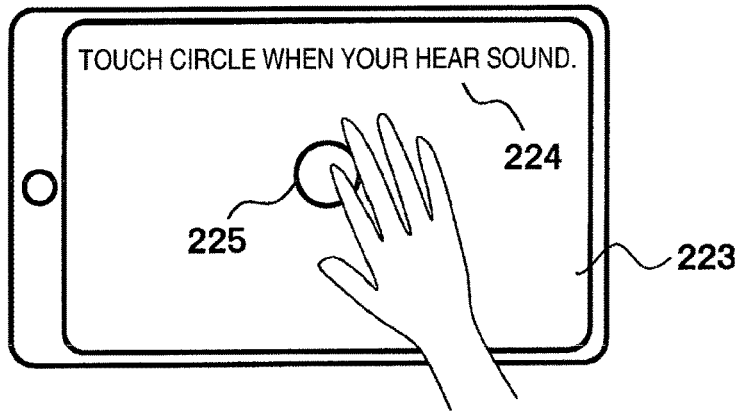
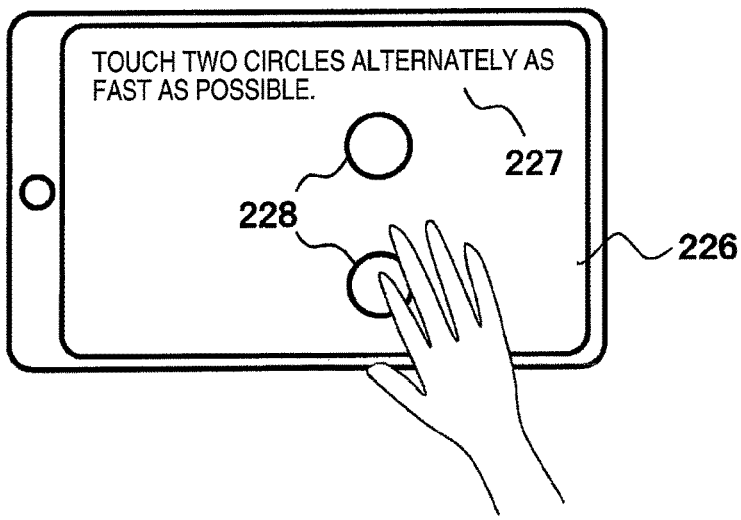

FIG. 24
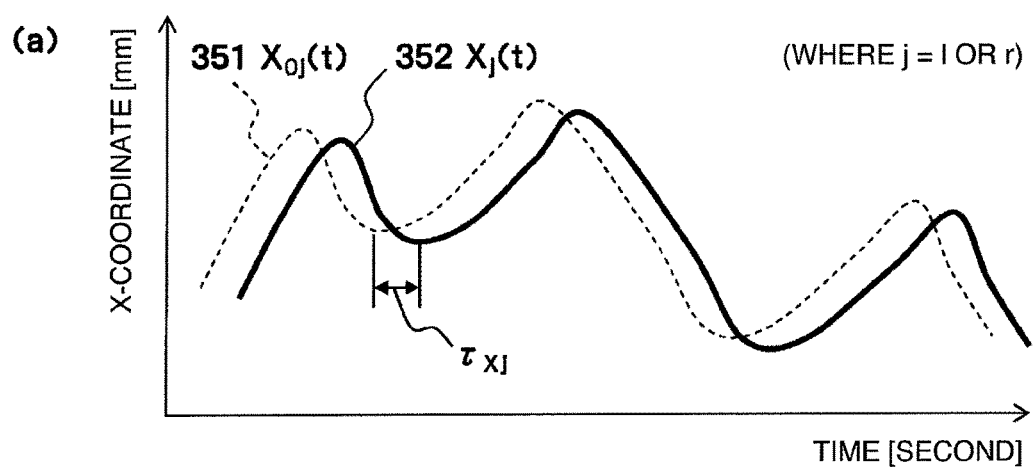
(a) 351 $X_{0j}(t)$  352 $X_j(t)$  (WHERE j = l OR r)
X-COORDINATE [mm]
$\tau_{Xj}$
TIME [SECOND]
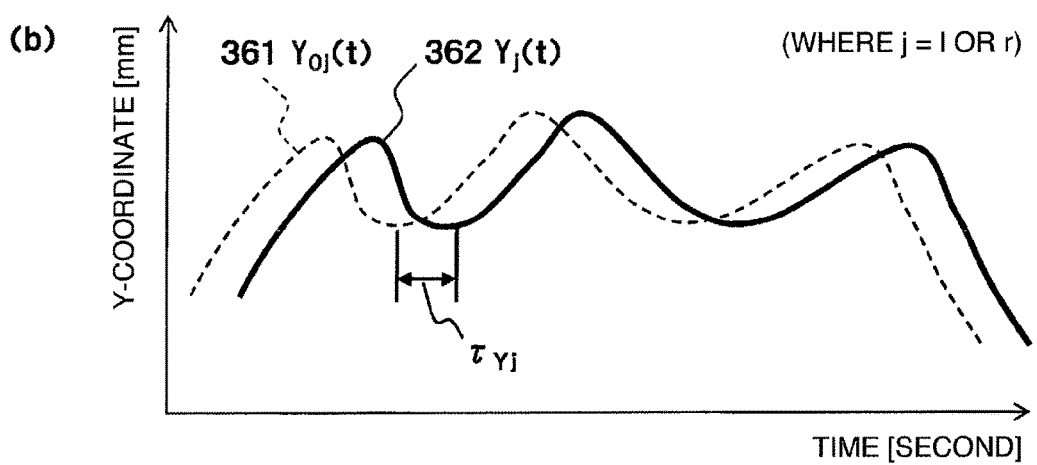
(b) 361 $Y_{0j}(t)$  362 $Y_j(t)$  (WHERE j = l OR r)
Y-COORDINATE [mm]
$\tau_{Yj}$
TIME [SECOND]

BRAIN DYSFUNCTION ASSESSMENT METHOD, BRAIN DYSFUNCTION ASSESSMENT DEVICE, AND PROGRAM THEREOF

TECHNICAL FIELD

The present invention relates to a technique for evaluating the degree of a brain dysfunction, or cerebral dysfunction such as a cognitive function decline.

BACKGROUND ART

In recent years, the number of dementia patients has increased as the aging of society advances. Nowadays, as much as two millions of patients in the country are estimated to be suffering from dementia. Dementia causes memory impairment, disorientation, learning impairment and the like that considerably interfere with everyday activities. In addition, problematic behavior such as ranting, violence, wandering, and dirty behavior may be seen in some cases. Furthermore, at a late stage, mobility impairments such as brachybasia and forward-bent posture are exhibited. Finally, dementia patients end up in a bedridden state.

In addition to three major dementias, i.e., Alzheimer's dementia, cerebrovascular dementia, and Lewy body dementia, dementia includes mobility impairment such as Parkinson's disease. Furthermore, in another case of dementia, a cognitive function declines in conjunction with mental disorder such as depression and schizophrenia. If the type of dementia can be determined by diagnosis, medical treatment appropriate for the determined type, such as medicinal treatment, can be then provided. In any type of dementia, early detection and appropriate medication can restrain progress from a mild state. In view of these aspects, a screening test for detecting dementia at an early stage needs to be conducted on healthy older people who are highly likely to become demented.

Major diagnosis for dementia is conducted by a test for checking a cognitive function such as memory and judgment, as in the Hasegawa's Dementia Scale and mini mental state examination (MMSE). Nevertheless, these diagnostic approaches require several minutes through several tens of minutes of face-to-face examination by a doctor. Thus, these diagnostic approaches cannot be suitable for a screening test to be conducted on numerous patients.

In addition, diagnosis based on cerebral image measurement is conducted. For example, there is a method for screening for the presence of brain shrinkage using Computed Tomography (CT) or Magnetic Resonance Imaging (MRI), and a method for examining the accumulation status of amyloid beta, which is a causative substance of dementia, using Single Photon Emission Computed Tomography (SPECT) or Positron Emission Tomography (PET). Nevertheless, these kinds of cerebral image measurement need high test cost, and require long test time. Thus, such diagnosis cannot be suitable for a screening test to be conducted on numerous patients.

In light of these problems, for example, PATENT LITERATURE 1, PATENT LITERATURE 2, NON PATENT LITERATURE 1 and the like disclose examples of an evaluation system for easily evaluating a cognitive function of a subject without depending on a doctor, by using a tablet computer equipped with a touch panel sensor.

CITATION LIST

Patent Literatures

PATENT LITERATURE 1: JP-A-2012-217797
PATENT LITERATURE 2: JP-A-2011-083403

Non Patent Literature

NON PATENT LITERATURE 1: Robbins T. W., and five others, "Cambridge Neuropsychological Test Automated Battery (CANTAB): a factor analytic study of a large sample of normal elderly volunteers", Dementia and Geriatric Cognitive Disorders, Switzerland, 1994, Vol. 5, No. 5, pp. 266-281

SUMMARY OF INVENTION

Technical Problem

The simplified evaluation systems of a cognitive function disclosed in PATENT LITERATURE 1, PATENT LITERATURE 2, NON PATENT LITERATURE 1, and the like are systems for examining to what extent a subject memorizes the names, the shapes, and the number of objects displayed on a display screen and subsequently deleted. In other words, conventional evaluation systems of a cognitive function are biased toward the ones for evaluating memory or memory-related judgment of subjects. In particular, physical capabilities of subjects are tend not to be evaluated.

Generally, if a cognitive function is impaired, collaborative motions of extremities and body movements following an external stimulus are considered to become difficult. In addition, such a functional decline in body movements is likely to be observed at an early stage especially in hands and fingers that perform highly-dexterous movements. Thus, if the movements of hands and fingers are measured using an electronic device, dementia may be detected at an early stage based on the measurement result.

In view of the foregoing, the present invention aims to provide a cerebral dysfunction evaluation method and a cerebral dysfunction evaluation apparatus that can easily evaluate the degree of a cerebral dysfunction such as a cognitive function decline, and a program of the same.

Solution to Problem

A cerebral dysfunction evaluation method according to the present invention in which a data processing device connected to a body movement presenting device for presenting a body movement to be executed by a subject, and to a body movement detection sensor for detecting body movement data of a body movement executed by the subject according to the presented body movement, executes: a body movement instruction step of generating body movement instruction data of a body movement to be executed by the subject, and presenting a body movement that is based on the generated body movement instruction data, via the body movement presenting device to the subject, to instruct execution of the body movement; a body movement data acquisition step of chronologically acquiring, via the body movement detection sensor, body movement data of a body movement executed by the subject; a body movement accuracy calculation step of calculating a positional accuracy and a time-series accuracy of a body movement of the subject based on the body movement instruction data and the body movement data; and a cognitive impairment degree evaluation step of evaluating a cognitive impairment degree of the subject by comparing a value indicating an accuracy of a body movement of the subject that is obtained from the calculated positional accuracy and time-series accuracy, with statistical data indicating an accuracy of a body movement of a healthy subject that has been acquired in advance.

Advantageous Effects of Invention

According to the present invention, there can be provided a cerebral dysfunction evaluation method and a cerebral dysfunction evaluation apparatus that can easily evaluate the degree of a cerebral dysfunction such as a cognitive function decline, and a program of the same.

BRIEF DESCRIPTION OF DRAWINGS

FIG. 2 shows a diagram illustrating an example of a subject registration information display screen displayed when a cerebral dysfunction evaluation program is started up.

FIG. 3 shows a diagram illustrating an example of a body movement task selection screen displayed by a body movement task selection unit.

FIGS. 8(a) to 8(c) show diagrams illustrating examples of a calibration instruction screen presented on a body movement presenting device by a calibration unit. FIG. 8(a) illustrates an example of an instruction screen for visual calibration, FIG. 8(b) illustrates an example of an instruction screen for auditory calibration, and FIG. 8(c) illustrates an example of an instruction screen for physical capability calibration.

FIGS. 24(a) and 24(b) show diagrams illustrating a relationship between a position coordinate of a tracking target graphic and a touch position coordinate of a subject, as an example of a schematic temporal transitional change graph. FIG. 24(a) illustrates an example of a temporal transitional change of an X coordinate, and FIG. 24(b) illustrates an example of a temporal transitional change of a Y coordinate.

DESCRIPTION OF EMBODIMENTS

An embodiment for implementing the present invention (hereinafter, referred to as an "embodiment") will be described in detail below with reference to the drawings. In addition, in the embodiment described below, while a cerebral dysfunction is assumed to be a collective term generically referring to all the diseases that involve a so-called cognitive function decline (e g, Alzheimer's dementia, cerebrovascular dementia, Lewy body dementia, Parkinson's disease, hydrocephalia, depression, and schizophrenia), the cerebral dysfunction includes mobility impairment caused by cerebral stroke or the like. In addition, in the description of the embodiment, the cerebral dysfunction may be simply referred to as dementia.

1. Configuration of Cerebral Dysfunction Evaluation Apparatus 100

Figure 1:
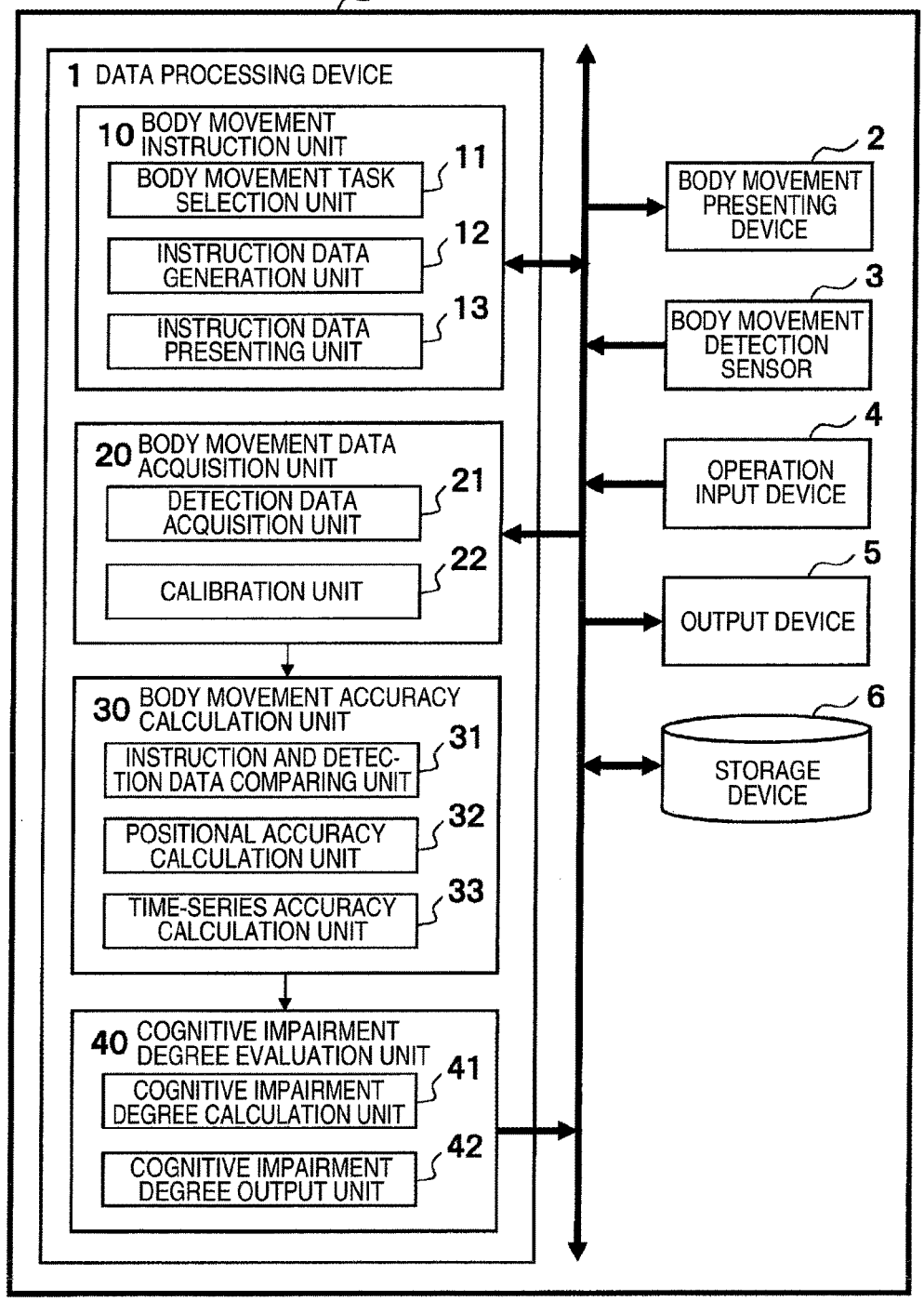
FIG. 1 shows a diagram illustrating an example of an entire configuration of a cerebral dysfunction evaluation apparatus according to an embodiment of the present invention.

FIG. 1 is a diagram illustrating an example of an entire configuration of a cerebral dysfunction evaluation apparatus 100 according to an embodiment of the present invention. As illustrated in FIG. 1, the cerebral dysfunction evaluation apparatus 100 according to the embodiment of the present invention includes a data processing device 1 with a central processing unit (CPU) (not shown) and a memory (not illustrated), a body movement presenting device 2, a body movement detection sensor 3, an operation input device 4, an output device 5, a storage device 6 and the like that are connected to the data processing device 1.

Here, the body movement presenting device 2 includes, for example, a liquid crystal display device, an audio output device (loudspeaker), and the like.

In addition, the body movement detection sensor 3 includes a touch panel sensor (screen contact-type sensor) attached to the above-described liquid crystal display device.

In addition, the operation input device 4 includes, for example, a keyboard, a mouse, and the like. The operation input device 4 may include a touch panel sensor. In such a case, the operation input device 4 may also serve as the body movement detection sensor 3.

In addition, the output device 5 includes, for example, a liquid crystal display device, a printer, and the like, and may also serve as the body movement presenting device 2.

In addition, the storage device 6 includes a hard disc device, a solid state disk (SSD), or the like, and stores data and programs that are determined to be prestored.

In addition, the data processing device 1 includes functional blocks such as a body movement instruction unit 10, a body movement data acquisition unit 20, a body movement accuracy calculation unit 30, and a cognitive impairment degree evaluation unit 40 that are implemented by the CPU (not illustrated) executing programs stored in the memory (not illustrated). In this case, the memory includes a random access memory (RAM) of a semiconductor memory, and the like. The programs to be executed are read from the storage device 6 and loaded into the memory as necessary. In addition, data being calculated is stored in the memory.

Next, the overview of the functional blocks constituting the data processing device 1 will be described (the detailed description will be given later).

The body movement instruction unit 10 includes, as subordinate functional blocks, a body movement task selection unit 11, an instruction data generation unit 12, an instruction data presenting unit 13, and the like.

The body movement task selection unit 11 displays, on the output device 5 (e.g., liquid crystal display device), a list of body movement tasks prepared in advance (refer to FIG. 3 described later). The body movement task selection unit 11 then selects a body movement task to be executed, based on an input operation performed on the operation input device 4 by a subject or a helper of the subject.

The instruction data generation unit 12 generates time-series body movement instruction data to be presented to the subject, according to the selected body movement task.

The instruction data presenting unit 13 presents, to the subject, the generated time-series body movement instruction data, i.e., the detail of a body movement to be executed by the subject, via the body movement presenting device 2 (e.g., liquid crystal display device and audio output device).

The body movement data acquisition unit 20 includes, as subordinate functional blocks, a detection data acquisition unit 21, a calibration unit 22, and the like.

The detection data acquisition unit 21 acquires, at a predetermined time interval (e.g., 10 milliseconds) via the body movement detection sensor 3 or the like, data of a body movement executed by the subject (e.g., a position of a specific portion of a body, movement speed, acceleration, detection time) according to the detail of the body movement presented on the body movement presenting device 2. In other words, the detection data acquisition unit 21 acquires time-series data of the body movement of the subject.

The calibration unit 22 acquires auditory capability data, visual capability data, and physical capability data that are independent of a cognitive impairment and specific to each subject. Based on the acquired data, the calibration unit 22 calculates calibration data for each subject, and stores the calculated calibration data into the storage device 6.

The body movement accuracy calculation unit 30 includes, as subordinate functional blocks, an instruction and detection data comparing unit 31, a positional accuracy calculation unit 32, a time-series accuracy calculation unit 33, and the like.

The instruction and detection data comparing unit 31 compares the data of the body movement that is to be executed by the subject and presented on the body movement presenting device 2 (e.g., liquid crystal display device), with data of a body movement that has been executed by the subject and acquired via the body movement detection sensor 3.

The positional accuracy calculation unit 32 calculates a positional accuracy of a body movement of the subject based on data of a difference between position instruction data and detection data of the body movement of the subject that has been acquired by the instruction and detection data comparing unit 31.

In addition, the time-series accuracy calculation unit 33 calculates a time-series accuracy of the body movement of the subject based on data of a difference between an instruction timing of the instruction data and a detection timing of the detection data that has been acquired by the instruction and detection data comparing unit 31.

The cognitive impairment degree evaluation unit 40 includes, as subordinate functional blocks, a cognitive impairment degree calculation unit 41, a cognitive impairment degree output unit 42, and the like.

The cognitive impairment degree calculation unit 41 calculates a cognitive impairment degree of the subject using the positional accuracy and the time-series accuracy that have been calculated by the body movement accuracy calculation unit 30, and furthermore, the calibration data acquired by the calibration unit 22, and the like.

Figure 9:
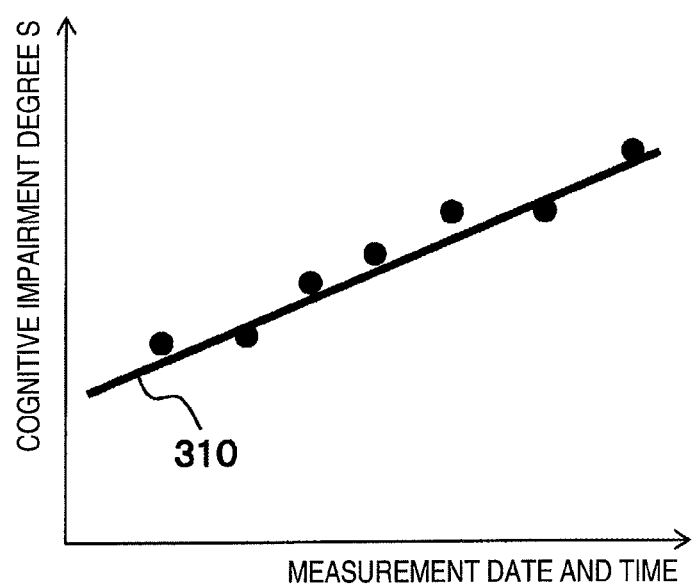
FIG. 9 shows a diagram illustrating an example of a chronological change graph of a cognitive impairment degree of a certain subject.

In addition, the cognitive impairment degree output unit 42 displays, on the output device 5 (e.g., liquid crystal display device), data of the cognitive impairment degree calculated by the cognitive impairment degree calculation unit 41, or chronological change data of the cognitive impairment degree (refer to FIG. 9 described later).

With the above-described configuration, the subject or the helper of the subject can recognize the cognitive impairment degree of the subject and the chronological change of the cognitive impairment degree.

In addition, the cerebral dysfunction evaluation apparatus 100 having the above-described configuration can be realized by a tablet computer equipped with a touch panel sensor, and a so-called tablet terminal, a smartphone, and the like that have functions and performance substantially equivalent to those of the tablet computer.

In addition, in the present embodiment, a touch panel sensor is used as the body movement detection sensor 3 so as to mainly detect movements of hands and fingers. Alternatively, a sensor for detecting a body movement of a portion other than hands and fingers may be used as the body movement detection sensor 3. In such a case, an acceleration sensor, a magnetic sensor, a gyroscopic device, a motion capture device, a video camera, or the like can be used the body movement detection sensor 3.

2. Configuration and Function of Data Processing Device 1

Subsequently, the functions of the functional blocks constituting the data processing device 1 will be described in detail. Hereinafter, in the present embodiment, the cerebral dysfunction evaluation apparatus 100 is assumed to be realized by a tablet computer or a tablet terminal that is equipped with a touch panel sensor, and a cerebral dysfunction evaluation program is assumed to be registered in the data processing device 1 thereof as an application program.

In addition, the cerebral dysfunction evaluation program includes respective programs for implementing the body movement instruction unit 10, the body movement data acquisition unit 20, the body movement accuracy calculation unit 30, and the cognitive impairment degree evaluation unit 40 of the data processing device 1.

2.1 Start-Up Processing

FIG. 2 is a diagram illustrating an example of a subject registration information display screen 110 displayed when the cerebral dysfunction evaluation program is started up. When the cerebral dysfunction evaluation program is started up in the data processing device 1 of the cerebral dysfunction evaluation apparatus 100 according to a predetermined operation, the subject registration information display screen 110 as illustrated in FIG. 2 (but fields on the right side are blank at first) is displayed on the output device 5 (liquid crystal display device).

The subject or the helper of the subject (hereinafter, referred to as "user") accordingly enters a subject identification data (ID) in a subject ID field. Then, if the entered subject ID is not registered in the storage device 6, the data processing device 1 prompts the user to enter data such as a subject name, gender, age, and remarks (for example, outputs a message for prompting the user to enter these kinds of data). Next, if the user enters the respective kinds of data in a subject name field, a gender field, an age field, a remarks field, and the like, the data processing device 1 registers the entered data including the subject name, the gender, the age, and the remarks, in the storage device 6 in association with the subject ID. In addition, the remarks field is a field in which the user can freely enter texts. For example, a disease name of the subject, a cognitive impairment degree diagnosed by a doctor when the subject is registered and the like are described in the remarks field.

On the other hand, if the entered subject ID has been already registered in the storage device 6, the data processing device 1 reads from the storage device 6 the data including the subject name, the gender, the age, and the remarks that are stored in association with the entered subject ID, and displays the respective kinds of read data with these kinds of data being described in the corresponding fields of the subject registration information display screen 110.

FIG. 3 is a diagram illustrating an example of a body movement task selection screen 120 displayed by the body movement task selection unit 11. As illustrated in FIG. 3, a list of body movement tasks is displayed on the body movement task selection screen 120, together with selection instruction fields for instructing whether to select the respective body movement tasks. By placing a check mark 121 in such a selection instruction field, the user selects a body movement task to be executed. In addition, FIG. 3 illustrates an example in which a reaching task is selected.

In addition, various parameters used for each body movement task can be set and displayed on the body movement task selection screen 120. In addition, examples of the parameter include a timeout time provided for the subject performing a response movement after the instruction data of the body movement is presented, a presentation time interval from when the response movement is performed by the subject to when instruction data of the next body movement is presented, a difficulty level defined according to the above-described timeout time and the presentation time.

2.2 Instruction of Body Movement and Acquisition of Body Movement Data

Figure 4:
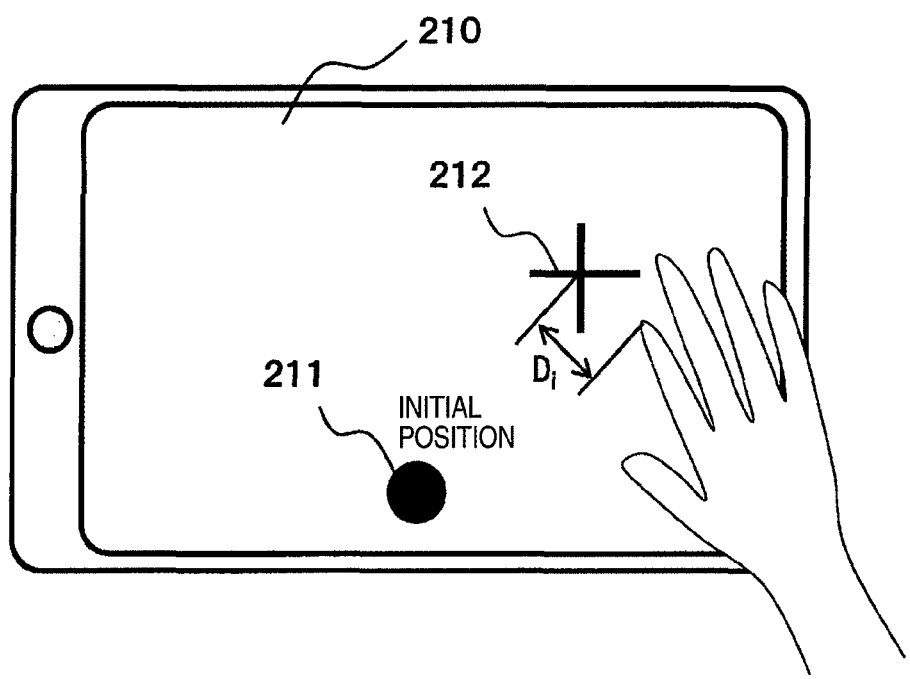
FIG. 4 shows a diagram illustrating an example of a reaching task instruction screen presented on a body movement presenting device by an instruction data presenting unit.

FIG. 4 is a diagram illustrating an example of a reaching task instruction screen 210 presented on the body movement presenting device 2 by the instruction data presenting unit 13. In the present embodiment, the instruction data presenting unit 13 of the data processing device 1 presents (displays) a graphic and a character on a display screen of a liquid crystal display device (the body movement presenting device 2) equipped with a touch panel sensor (the body movement detection sensor 3), according to each body movement task. The instruction data presenting unit 13 thereby instructs a position on the display screen that is to be touched by the subject, and a timing of the touch operation. The reaching task is a task for prompting, by presenting a specific graphic at a random position on the display screen, the subject to touch the presented specific graphic as fast as possible.

In the reaching task, the instruction data presenting unit 13 first displays, on the reaching task instruction screen 210, a black filled circle graphic 211 indicating an initial position. At this time, the subject places a finger on the black filled circle graphic 211 at the initial position, and holds steady. Next, the instruction data presenting unit 13 presents (displays) a cross-shaped graphic 212 on the reaching task instruction screen 210. In response to this, the subject releases the finger from the black filled circle graphic 211 where the finger has been on standby, and then touches the cross-shaped graphic 212 as fast as possible. In addition, in FIG. 4, a distance $D_i$ represents a distance (linear distance) between the center position of the cross-shaped graphic 212 and a position on the reaching task instruction screen 210 that has been touched by the subject.

When it is determined that the subject has touched the cross-shaped graphic 212, based on a touch position of the subject that has been acquired by the detection data acquisition unit 21, the instruction data presenting unit 13 changes a display color of the cross-shaped graphic 212 to inform the subject that the cross-shaped graphic 212 has been properly touched. In this case, if the subject touches a position within a predetermined distance (e.g., within 5 mm) from an intersection point of the cross-shaped graphic 212, it is determined that the subject has properly touched the cross-shaped graphic 212. In addition, in such a case, the subject may be informed whether the subject has properly touched the cross-shaped graphic 212, by sound output from an audio output device such as a loudspeaker.

In addition, when the subject has properly touched the cross-shaped graphic 212, or when the cross-shaped graphic 212 has not been touched and a timeout error occurs, the instruction data presenting unit 13 deletes the cross-shaped graphic 212 that has been displayed (presented) so far, and further presents (displays) a new cross-shaped graphic 212 at a different position. The subject touches again the newly-presented (displayed) cross-shaped graphic 212 as fast as possible. Such presentation of the cross-shaped graphic 212 and a touch operation by the subject are repeated a predetermined number of times.

In addition, in the above-described reaching task, the detection data acquisition unit 21 acquires a coordinate detected when a portion of a subject body such as, for example, a finger has touched the display screen, i.e., the touch panel sensor. In this case, the finger comes into surface contact with the touch panel sensor. At this time, the detection data acquisition unit 21 acquires a coordinate of, for example, a centroid position of a graphic on the contact surface, as a coordinate of a finger contact position.

In such a touch panel sensor, in many cases, a coordinate of each point on the display screen is generally defined with an origin position of a coordinate being set to a left corner of the display screen, and assuming that a traverse direction is an x-axis direction and a longitudinal direction is a y-axis direction. Nevertheless, the origin position may be set to other corners of the display screen, and may be set to the center of the display screen. Furthermore, the origin position may be set to any position inside or outside the display screen. In addition, the x-axis direction and the y-axis direction are not limited to the traverse direction and the longitudinal direction.

The detection data acquisition unit 21 acquires, as a basic function thereof, a coordinate (x, y) of a position touched by a finger of the subject. In addition, if a plurality of fingers (e.g., a thumb and an index finger) simultaneously touches the touch panel sensor, the detection data acquisition unit 21 acquires a plurality of coordinates (e.g., (x1, y1), and (x2, y2)) corresponding to the respective finger contact positions. Furthermore, the detection data acquisition unit 21 acquires a time-series coordinate (x (t), y (t)) of a finger contact position at every predetermined timing cycle (e.g., 10 milliseconds).

Figure 5:
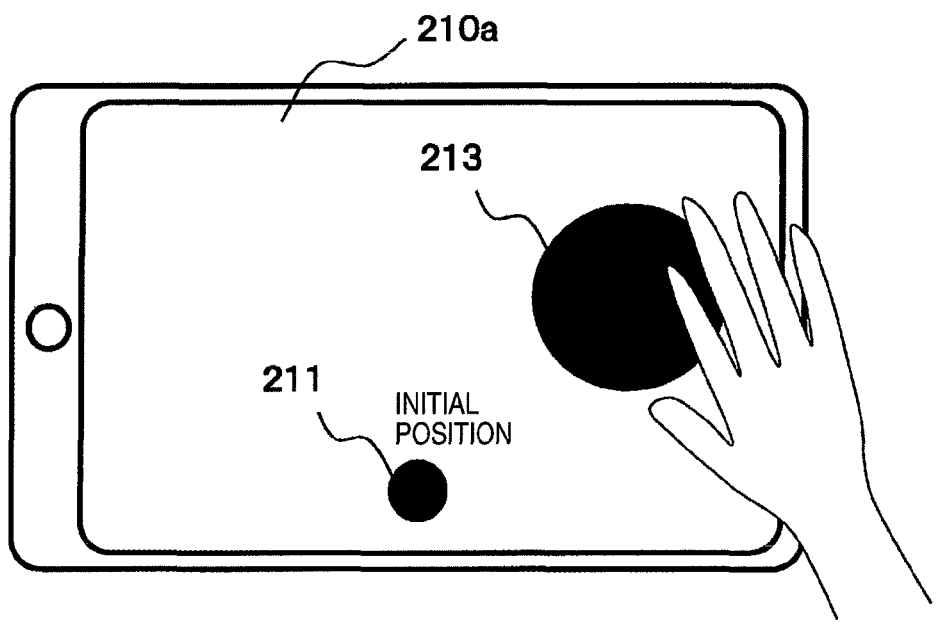
FIG. 5 shows a diagram illustrating a modified example of a reaching task instruction screen presented on a body movement presenting device by an instruction data presenting unit.

FIG. 5 is a diagram illustrating a modified example of the reaching task instruction screen 210 presented on the body movement presenting device 2 by the instruction data presenting unit 13. As illustrated in FIG. 5, a circular graphic 213 is presented on a reaching task instruction screen 210a according to the modified example, instead of the cross-shaped graphic 212. Except for this point, the processing performed by the instruction data presenting unit 13 and an operation executed by the subject are basically the same as those in the case of the reaching task instruction screen 210 illustrated in FIG. 4.

On the reaching task instruction screen 210a illustrated in FIG. 5, the instruction data presenting unit 13 may randomly change the size (radius) of the circular graphic 213 every time the instruction data presenting unit 13 presents the circular graphic 213.

In addition, in the case of healthy people, it is known as the Fitts's law that there is a definite relationship between a time required for reaching and the radius of the circular graphic 213. Thus, if the above-described reaching task is performed with various radii of the circular graphic 213 using the reaching task instruction screen 210a, it can be examined based on the result of the reaching task whether the relationship according to the Fitts's law is maintained even if a cerebral function such as a cognitive function declines.

Further modification of the reaching task is also available. In the above-described reaching tasks, the subject is supposed to unconditionally touch a graphic presented on the display screen. Alternatively, a certain determination condition may be imposed on the subject, and the subject may be prompted to perform a touch operation according to the determination result.

For example, the instruction data presenting unit 13 presents on the display screen a reference circle and a reaching target circle, to prompt the subject to compare the sizes of the two circles. Based on the comparison, the subject is supposed to touch the circle when the sizes of the two circles are the same, and not to touch the circle when the sizes of the two circles are different from each other. Alternatively, a condition for a touch operation may be defined not based on the size of a graphic to be presented, but the color or shape of the graphic. Yet alternatively, a condition for a touch operation may be defined based on the type of a presented character. For example, the subject is supposed to perform a touch operation when a hiragana character is displayed, and not to perform a touch operation when a katakana character or an alphabetical character is presented.

Furthermore, a conceptual determination condition may be imposed on the subject. For example, the instruction data presenting unit 13 presents a colored graphic and a color name on the display screen. In this case, the subject is supposed to perform a touch operation when the color name of the presented graphic and the presented color name are the same, and not to perform a touch operation when these color names are different from each other.

As described above, by the reaching task with a determination condition imposed on the subject, not only a simple movement function, but also a higher-level cognitive function of the subject can be evaluated.

2.3 Calculation of Body Movement Accuracy

When the reaching task as illustrated in FIG. 4 or 5 is executed, the detection data acquisition unit 21 acquires a coordinate (X, Y) of a position touched by the subject, and time-series data about a time t. Hereinafter, in this specification, the coordinate (X, Y) and the time-series data of the time t will be represented as $(X_i(t_i), Y_i(t_i))$, or simply (X (t), Y (t)), where i=1, 2, . . . , N, and N represents the number of reaching repetitions.

The instruction and detection data comparing unit 31 first calculates, for each presented reaching target graphic, a distance between a center position $(XC_i(\tau_i), YC_i(\tau_i))$ of the graphic and a position $(X_i(t_i), Y_i(t_i))$ touched by the subject, as a touch position error $D_i$ (refer to FIG. 4). Furthermore, the instruction and detection data comparing unit 31 calculates, for each presented reaching target graphic, a difference between a time $\tau_i$ when the graphic has been displayed and a time $t_i$ when the subject has performed a touch operation, as a touch delay time $\tau_i$.

A positional accuracy and a time-series accuracy can be assumed as the accuracy of a body movement.

The positional accuracy refers to a matching degree of the position touched by the subject, with respect to the position of the graphic presented by the instruction data presenting unit 13. Thus, in the case of a reaching task, a positional accuracy $m_d$ can be defined as, for example, an average value $(=\Sigma D_i/N)$ of touch position errors $D_i$ calculated by the instruction and detection data comparing unit 31, and is calculated by the positional accuracy calculation unit 32.

In addition, the time-series accuracy refers to a matching degree of the time $t_i$ when the subject has performed a touch operation, with respect to the time $\tau_i$ when the reaching target graphic has been presented by the instruction data presenting unit 13. Thus, in the case of a reaching task, a time-series accuracy $m_T$ can be defined as an average value ($=\Sigma T_i/N$) of touch delay times $\tau_i$ calculated by the instruction and detection data comparing unit 31, and is calculated by the time-series accuracy calculation unit 33.

In addition, in this specification, a smaller value of the accuracy (positional accuracy $m_d$ or time-series accuracy $m_T$) indicates a higher matching degree between instruction data of a body movement and data obtained based on an actual movement of the subject.

2.4 Evaluation of Cognitive Impairment Degree

A cognitive impairment degree S is calculated as an integrated value of a positional accuracy $m_d$ calculated by the positional accuracy calculation unit 32 and a time-series accuracy $m_T$ calculated by the time-series accuracy calculation unit 33. As a method for calculating the cognitive impairment degree S, there are various methods as described below. Any of the following methods may be used.

(First Calculation Method of Cognitive Impairment Degree S)

The simplest calculation method of the cognitive impairment degree S is a method of normalizing a positional accuracy $m_d$ and a time-series accuracy $m_T$, and simply summing up both of the normalized accuracies.

In this calculation, the following values are used for the normalization of the positional accuracy $m_d$: an average $M_C$ ($m_{dj}$) and a standard deviation $\sigma_C$ ($m_{dj}$) of positional accuracies $m_{dj}$ (j=1, 2, ..., P: P represents the number of subjects in a healthy group) that have been obtained from a plurality of subjects in the healthy group by executing a similar reaching task on the plurality of subjects in the healthy group in advance. In addition, the following values are used for the normalization of the time-series accuracy $m_T$: an average value $M_C$ ($m_{Tj}$) and a standard deviation $\sigma_C$ ($m_{Tj}$) of time-series accuracies $m_{Tj}$ (j=1, 2, ..., P: P represents the number of subjects in a healthy group) of a plurality of subjects that have been obtained from the above-described reaching task executed on the plurality of subjects in the healthy group in advance.

In addition, the average value $M_C$ ($m_{dj}$) and the standard deviation $\sigma_C$ ($m_{dj}$) of the positional accuracies $m_{dj}$, and the average value $M_C$ ($m_{Tj}$) and the standard deviation $\sigma_C$ ($m_{Tj}$) of the time-series accuracies $m_{Tj}$ that are to be obtained from the healthy group and to be used in the normalizations are pre-calculated and prestored in the storage device 6.

Thus, the cognitive impairment degree calculation unit 41 first calculates a normalized positional accuracy $m_{d\_n}$ and a normalized time-series accuracy $m_{T\_n}$ according to the following Formulae (1) and (2).

[MATH. 1]

$$m_{d\_n}=(m_d-M_c(m_{dj}))/\sigma_c(m_{dj}) \quad (1)$$

$$m_{T\_n}=(m_T-M_c(m_{Tj}))/\sigma_c(m_{Tj}) \quad (2)$$

Subsequently, the cognitive impairment degree calculation unit 41 calculates the cognitive impairment degree S according to the following Formula (3). In other words, the cognitive impairment degree S is calculated as a value obtained by simply summing up the normalized positional accuracy $m_{d\_n}$ and the normalized time-series accuracy $m_{T\_n}$.

[MATH. 2]

$$S=m_{d\_n}+m_{T\_n} \quad (3)$$

(Second Calculation Method of Cognitive Impairment Degree S)

As the second method, the cognitive impairment degree S may be calculated by weighing the positional accuracy $m_d$ and the time-series accuracy $m_T$ according to respective importance degrees, and summing up the weighted values. In this case, when the respective weights of the positional accuracy $m_d$ and the time-series accuracy $m_T$ are represented as $I_d$ and $I_T$, the cognitive impairment degree S can be calculated according to the following Formula (4).

[MATH. 3]

$$S=I_d m_d + I_T m_T \quad (4)$$

The weights $I_d$ and $I_T$ can be calculated according to the following Formulae (5) and (6), for example.

In the calculations, the following values are assumed to be already obtained, and stored in the storage device 6: an average value $M_C$ ($m_{dj}$) and a standard deviation $\sigma_C$ ($m_{dj}$) of positional accuracies $m_{dj}$, and an average value $M_C$ ($m_{Tj}$) and a standard deviation $\sigma_C$ ($m_{Tj}$) of time-series accuracies $m_{Tj}$ of $P_C$ subjects in a healthy group; and furthermore, an average value $M_P$ ($m_{dk}$) and a standard deviation $\sigma_P$ ($m_{dk}$) of positional accuracies $m_{dk}$, and an average value $M_P$ ($m_{Tk}$) and a standard deviation $\sigma_P$ ($m_{Tk}$) of time-series accuracies $m_{Tk}$ of $P_P$ subjects in a dementia group, where j=1, 2, ..., $P_C$, and k=1, 2, ..., $P_P$.

[MATH. 4]

$$I_d = \frac{|M_P(m_{dk}) - M_C(m_{dj})|}{\sqrt{\frac{\sigma_P(m_{dk})^2}{P_P} + \frac{\sigma_C(m_{dj})^2}{P_C}}} \quad (5)$$

$$I_T = \frac{|M_P(m_{Tk}) - M_C(m_{Tj})|}{\sqrt{\frac{\sigma_P(m_{Tk})^2}{P_P} + \frac{\sigma_C(m_{Tj})^2}{P_C}}} \quad (6)$$

These weights $I_d$ and $I_T$ are indices for evaluating the degree of the difference between the respective average values of the healthy group and the dementia group considering the variations in the healthy group and the dementia group, and defined with reference to the statistics that are used in the Welch's test (a method of testing the presence or absence of the difference between the respective average values of two groups in a case where the two groups are different from each other in variance).

According to Formula (5), a larger weight $I_d$ means a larger difference in positional accuracy $m_d$ between the two groups. This means that it is easy to determine which of the two groups a subject belongs to, based on the positional accuracy $m_d$. In other words, the positional accuracy $m_d$ can be considered as an index important for detecting the dementia group more easily as the weight $I_d$ increases. In addition, according to Formula (6), the time-series accuracy $m_T$ can be similarly considered as an index important for detecting the dementia group more easily as the weight $I_T$ increases.

In addition, the calculations of the weights $I_d$ and $I_T$ are not limited to those according to Formulae (5) and (6). Another statistic may be used as long as the degree of the difference between the healthy group and the dementia group can be evaluated using the statistic.

As described above, in the second calculation method of the cognitive impairment degree S, the cognitive impairment degree calculation unit 41 calculates the cognitive impairment degree S by performing calculations according to Formulae (5) and (6), and further performing calculation according to Formula (4). In addition, it is preferable to prestore the weights $I_d$ and $I_T$ in the storage device 6, rather than calculating every time the calculation is performed.

(Third Calculation Method of Cognitive Impairment Degree S)

Figure 6:
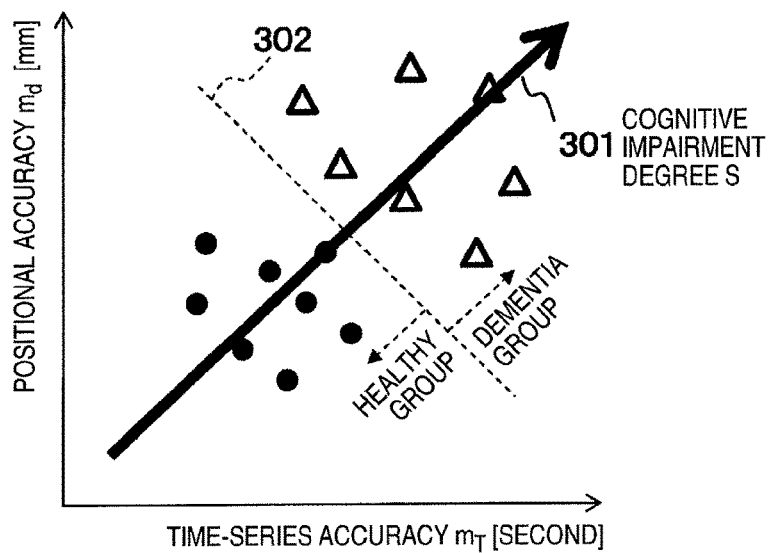
FIG. 6 shows a diagram schematically illustrating an example of evaluating a cognitive impairment degree using multivariate analysis.

Furthermore, as another example of evaluating the cognitive impairment degree S, an example of using multivariate analysis will be described. FIG. 6 is a diagram schematically illustrating an example of evaluating the cognitive impairment degree S using the multivariate analysis. In other words, a graph illustrated in FIG. 6 indicates, as a scatter diagram, a time-series accuracy $m_T$ and a positional accuracy $m_d$ of each subject with a time-series accuracy $m_T$ (an average touch delay time) on a horizontal axis and a positional accuracy $m_d$ (an average touch position error) on a vertical axis.

In the scatter diagram illustrated in FIG. 6, black filled circle marks indicate time-series accuracies $m_T$ and positional accuracies $m_d$ of a plurality of subjects belonging to the healthy group, and triangular marks indicate time-series accuracies $m_T$ and positional accuracies $m_d$ of a plurality of subjects belonging to the dementia group.

In addition, in the example illustrated in FIG. 6, only two types of variable amounts, i.e., a positional accuracy $m_d$ as an average touch position error and a time-series accuracy $m_T$ as an average touch delay time are assumed to be analyzed. Nevertheless, as variable amounts to be analyzed, other feature amounts indicating a positional accuracy, a time-series accuracy, and the like may be added as appropriate.

If linear discriminant analysis, which is one type of the multivariate analysis, is applied to the data of the scatter diagram illustrated in FIG. 6, an axis 301 indicating the cognitive impairment degree S can be obtained. In addition, the cognitive impairment degree S is represented by the following Formula (7) using coefficients $C_{d1}$ and $C_{T1}$ obtained by the linear discriminant analysis.

[MATH. 5]

$$S = C_{d1} m_d + C_{T1} m_T \quad (7)$$

Thus, if the time-series accuracy $m_T$ and the positional accuracy $m_d$ of a subject can be obtained through a reaching task or the like, the cognitive impairment degree S can be calculated based on the obtained axis 301, i.e., Formula (7).

Furthermore, as illustrated in FIG. 6, a straight line 302 (displayed as a broken line in FIG. 6) perpendicularly intersecting with the axis 301 at a certain threshold $S_{th}$ can be used as a borderline for separating the healthy group and the dementia group. In other words, if the cognitive impairment degree S of a subject that is obtained according to Formula (7) is larger than the threshold $S_{th}$, the subject can be determined to be dementia. If the cognitive impairment degree S is not larger than the threshold $S_{th}$, the subject can be determined to be not dementia. In addition, in the determination, if the threshold $S_{th}$ is set to a smaller value close to the healthy group, dementia can be detected in a more sensitive manner. If the threshold $S_{th}$ is set to a larger value close to the dementia group, the erroneous detection of dementia can be avoided.

As described above, in the third calculation method of the cognitive impairment degree S, the cognitive impairment degree calculation unit 41 calculates the coefficients $C_{d1}$ and $C_{T1}$ in advance using the linear discriminant analysis or the like, and when the time-series accuracy $m_T$ and the positional accuracy $mm_d$ of a subject are obtained, calculates the cognitive impairment degree S of the subject according to Formula (7).

In addition, in the above example, the description has been given of a method of using the linear discriminant analysis for calculating the cognitive impairment degree S. Alternatively, the cognitive impairment degree S may be calculated using another statistical method such as a support vector machine, as long as the method can discriminate between two groups based on a plurality of feature amounts, and convert the degree of a difference therebetween into a number.

Figure 7:
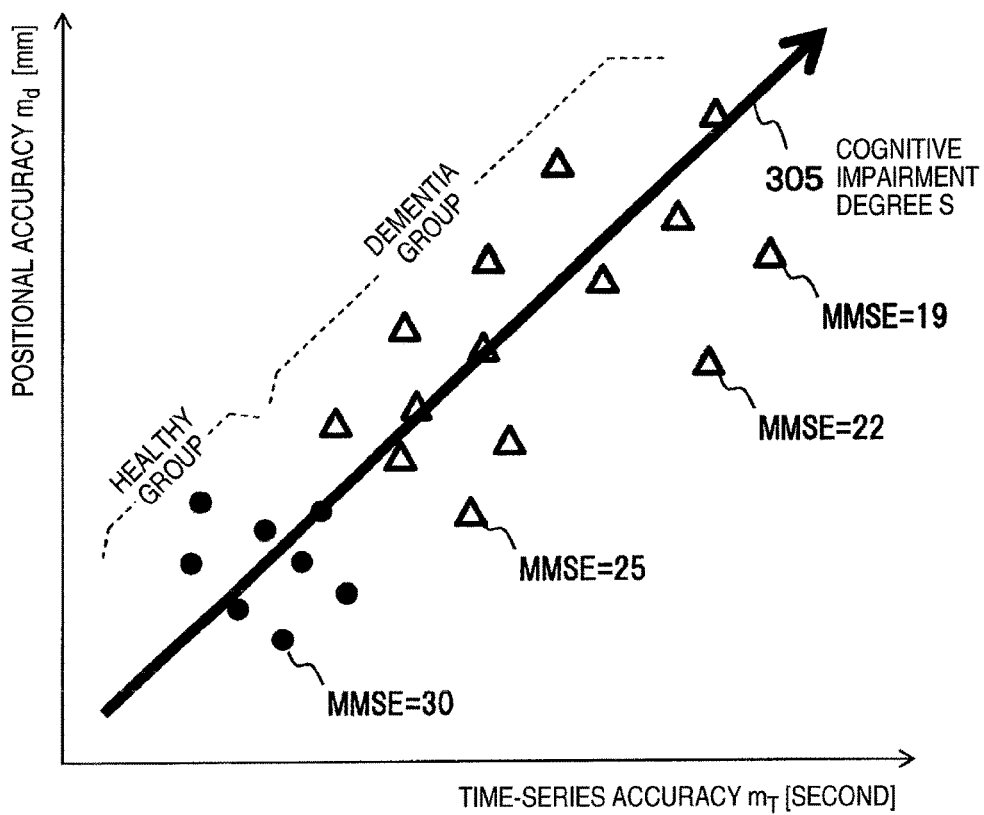
FIG. 7 shows a diagram schematically illustrating a modified example of the example of evaluating a cognitive impairment degree S illustrated in FIG. 6.

FIG. 7 is a diagram schematically illustrating a modified example of the example of evaluating the cognitive impairment degree S that is illustrated in FIG. 6. In a similar manner to the scatter diagram illustrated in FIG. 6, a scatter diagram illustrated in FIG. 7 indicates data (black filled circle marks and triangular marks) of respective pluralities of subjects belonging to the healthy group and the dementia group. In addition, in FIG. 7, data of each subject is assigned a score of mini mental state examination (MMSE) obtained by evaluating the degree of dementia in advance through medical examination conducted by a doctor.

In addition, in the MMSE, the highest score of 30 indicates a healthy state without a cognitive function decline, and a lower score indicates more severe dementia. If multiple linear regression analysis, which is one type of the multivariate analysis, is applied to positional accuracies $m_d$, time-series accuracies $m_T$, and scores of the MMSE of this healthy group, an axis 305 indicating the cognitive impairment degree S can be obtained. In addition, the cognitive impairment degree S is represented by the following Formula (8) using coefficients $C_{d2}$ and $C_{T2}$ obtained by the multiple linear regression analysis.

[MATH. 6]

$$S = C_{d2} m_d + C_{T2} m_T \quad (8)$$

In addition, this Formula (8) can be regarded as a formula for estimating a score of the MMSE that is evaluated by a doctor, based on the time-series accuracy $m_T$ and the positional accuracy $m_d$.

Thus, in a similar manner to the case of the example illustrated in FIG. 6, the cognitive impairment degree calculation unit 41 calculates the coefficients $C_{d2}$ and $C_{T2}$ in advance using the multiple linear regression analysis or the like, and when the time-series accuracy $m_T$ and the positional accuracy $m_d$ of a subject are obtained, calculates the cognitive impairment degree S of the subject according to Formula (8).

2.5 Calibration

The calibration unit 22 evaluates the capabilities of a subject such as an auditory capability, a visual capability, and a physical capability in advance, and subtracts the influences of these capabilities that are to be exerted on a task for evaluating the cognitive impairment degree S (a reaching task in the present embodiment). In this case, all the influences including those of the auditory capability, the visual capability, and the physical capability may be subtracted, or only any one of them may be subtracted.

FIGS. 8(a) to 8(c) are diagrams illustrating examples of a calibration instruction screen presented on the body movement presenting device 2 by the calibration unit 22. FIG. 8(a) illustrates an example of an instruction screen for visual calibration, FIG. 8(b) illustrates an example of an instruction screen for auditory calibration, and FIG. 8(c) illustrates an example of an instruction screen for physical capability calibration.

In the case of evaluating a visual capability of a subject, for example, the calibration unit 22 displays a calibration instruction message 221 and a cross-shaped graphic 222 on a calibration instruction screen 220 as illustrated in FIG. 8(a). Next, the calibration unit 22 prompts the subject to touch the center (an intersection point) of the cross-shaped graphic 222 without imposing any time restriction, and acquires a distance $D_i$ between the position touched by the subject and the center of the cross-shaped graphic 222.

Furthermore, the calibration unit 22 prompts the subject to perform a similar operation a plurality of times (n times), and calculates the average of the distances $D_i$ (i=1, 2, ... n), i.e., an average value of touch position errors as a position calibration value $c_d$ of the subject. Then, by subtracting this position calibration value $c_d$ from the positional accuracy $m_d$ of the subject that has been obtained by the positional accuracy calculation unit 32, a calibrated positional accuracy $m_{dc}$ (=$m_d$-$c_d$), in which the influence of the visual capability of the subject has been canceled, is obtained.

For example, when the position calibration value $c_d$ of the subject is 3 mm, and the positional accuracy $m_d$ obtained through the reaching task or the like is 10 mm, the calibrated positional accuracy $m_{dc}$ is 7 mm.

In addition, in the case of evaluating an auditory capability of a subject, for example, the calibration unit 22 displays a calibration instruction message 224 and a circular graphic 225 on a calibration instruction screen 223 as illustrated in FIG. 8(b). Next, the calibration unit 22 outputs predetermined sound from a loudspeaker or the like, and prompts the subject to touch the circular graphic 225 when the subject hears the sound. The calibration unit 22 thereby acquires a touch delay time which is a time from when the sound is output to when the subject touches the circular graphic 225.

Furthermore, the calibration unit 22 prompts the subject to perform a similar operation a plurality of times (n times), and calculates an average value of touch delay times $t_i$ (i=1, 2, ..., n) as a time-series calibration value $c_T$ that is based on the auditory capability of the subject. Then, by subtracting this time-series calibration value $c_T$ from the time-series accuracy $m_T$ of the subject that has been obtained by the time-series accuracy calculation unit 33, a calibrated time-series accuracy $m_{Tc}$ (=$m_T$-$c_T$), in which the influence of the auditory capability of the subject has been canceled, is obtained.

For example, when the time-series calibration value $c_T$ that is based on the auditory capability of the subject is 60 milliseconds, and the time-series accuracy $m_T$ obtained through a task related to an auditory capability, such as a rhythm touch task to be described later, is 100 milliseconds, the calibrated time-series accuracy $m_{Tc}$ is 40 milliseconds.

In addition, in the case of evaluating a physical capability of a subject, for example, the calibration unit 22 displays a calibration instruction message 227 and two circular graphics 228 on a calibration instruction screen 226 as illustrated in FIG. 8(c). The calibration unit 22 prompts the subject to alternately touch as fast as possible the two circular graphics 228 displayed at determined positions, and acquires a time interval t, at which the two circular graphics 228 are alternately touched.

The calibration unit 22 prompts the subject to perform an alternate touch operation a plurality of times (n times), and calculates an average value of alternate touch time intervals $t_i$ (i=1, 2, ..., n) as a time-series calibration value $e_T$ that is based on the physical capability of the subject. Then, by subtracting this time-series calibration value $e_T$ from the time-series accuracy $m_T$ of the subject that has been obtained by the time-series accuracy calculation unit 33, a calibrated time-series accuracy $m_{Te}$ (=$m_T$-$e_T$), in which the influence of the physical capability of the subject has been canceled, is obtained.

For example, when the time-series calibration value $e_T$ that is based on the physical capability of the subject is 80 milliseconds, and the time-series accuracy $m_T$ obtained through the reaching task or the like is 100 milliseconds, the calibrated time-series accuracy $m_{Te}$ is 20 milliseconds. In addition, 20 milliseconds in this case indicates a time taken for the subject recognizing the position of a graphic to be reached (the cross-shaped graphic 212 in the example illustrated in FIG. 4).

As described above, by evaluating an auditory capability, a visual capability, and a physical capability of a subject in advance, the calibration unit 22 can calibrate, according to the auditory capability, the visual capability, and the physical capability of the subject, the positional accuracy $m_d$ and the time-series accuracy $m_T$ that are to be obtained through the task for evaluating the cognitive impairment degree S. In addition, the values of the calibrated positional accuracy $m_{de}$ and the calibrated time-series accuracies $m_{Tc}$ and $m_{Te}$ that have been obtained by the calibration unit 22 are used as the values of the positional accuracy $m_d$ and the time-series accuracy $m_T$ in the subsequent processing for calculating the cognitive impairment degree S that is to be performed by the cognitive impairment degree calculation unit 41.

As described above, by using the calibration unit 22, highly-accurate positional accuracy $m_d$ and time-series accuracy $m_T$ can be obtained considering an auditory capability, a visual capability, and a physical capability of a subject. This enables more accurate calculation of the cognitive impairment degree S.

2.6 Storage and Display of Evaluation Result

The cognitive impairment degree output unit 42 stores the cognitive impairment degree S calculated by the cognitive impairment degree calculation unit 41, into the storage device 6. At this time, not only the cognitive impairment degree S, but also a measurement date and time, a subject ID, the age and gender of a subject, and the like can be desirably stored together. Furthermore, a score of the MMSE, frontal assessment battery (FAB), the Hasegawa's Dementia Scale, or the like that has been obtained through a medical interview conducted by a doctor may be stored together.

The cognitive impairment degree output unit 42 outputs the cognitive impairment degree S calculated by the cognitive impairment degree calculation unit 41, to the output device 5 such as a liquid crystal display device and a printer. Thus, the subject or the helper of the subject can recognize the cognitive impairment degree S of the subject that has been obtained through an executed cognitive impairment degree evaluation task such as the reaching task.

The cognitive impairment degree output unit 42 displays a chronological change graph indicating a relationship between the measurement date and time and the cognitive impairment degree S of the subject that are stored in the storage device. FIG. 9 is a diagram illustrating an example of a chronological change graph of the cognitive impairment degree S of a certain subject. In the graph illustrated in FIG. 9, a horizontal axis indicates a date and time when the subject has performed the reaching task and the like, that is, a date and time when the cognitive impairment degree S of the subject has been measured. In addition, a vertical axis indicates the cognitive impairment degree S. In addition, black filled circle marks indicate cognitive impairment degrees S of the certain subject that have been obtained at respective measurement dates and times.

The cognitive impairment degree output unit 42 further obtains a chronological change index $S_d$ of the cognitive impairment degree S of the certain subject. Here, the chronological change index $S_d$ of the cognitive impairment degree S can be represented as, for example, the inclination of a straight line 310 drawn in the graph in FIG. 9. The inclination of the straight line 310 can be obtained by regression analysis, a least-square method, or the like.

In this case, the chronological change index $S_d$ of the cognitive impairment degree S being smaller than 0 means that cognitive impairment is getting worse. The index $S_d$ being approximately equal to 0 means that worsening advance of the cognitive impairment is at a stop. The index $S_d$ being larger than 0 means that the cognitive impairment is getting better. Thus, a doctor, the subject, and a helper can recognize, from the graph indicating the chronological change of the cognitive impairment degree S as illustrated in FIG. 9, the effect and the like of medical treatment or rehabilitation being executed on the subject.

In addition, the chronological change index $S_d$ of the cognitive impairment degree S is not limited to the inclination of the straight line 310. Another index may be used as long as the chronological change of the cognitive impairment degree S between the present time and past can be evaluated using the index. For example, the standard deviation of the cognitive impairment degrees S of past several times may be used as the chronological change index $S_d$ of the cognitive impairment degree S. In this case, a sort of stability of a cognitive function is evaluated.

According to the embodiment of the present invention described above, the degree (the cognitive impairment degree S) of a cognitive function decline including cerebral dysfunction of a subject can be easily evaluated. Furthermore, the effect and the like of medical treatment or rehabilitation being executed on the subject can be recognized.

3. Modified Example of Body Movement Task

In the embodiment described so far, the cognitive impairment degree S is calculated based on a result obtained by a subject executing the reaching task. Alternatively, the cognitive impairment degree S may be calculated based on a result obtained by a subject executing another body movement task. Hereinafter, an example of another body movement task for obtaining the cognitive impairment degree S will be described. In addition, if a method for calculating the cognitive impairment degree S is different from that in the above-described embodiment of the reaching task, the different point will be also described.

3.1 Rhythm Touch Task (a. Auditory Stimulus-Based Rhythm Touch Task)

Figure 10:
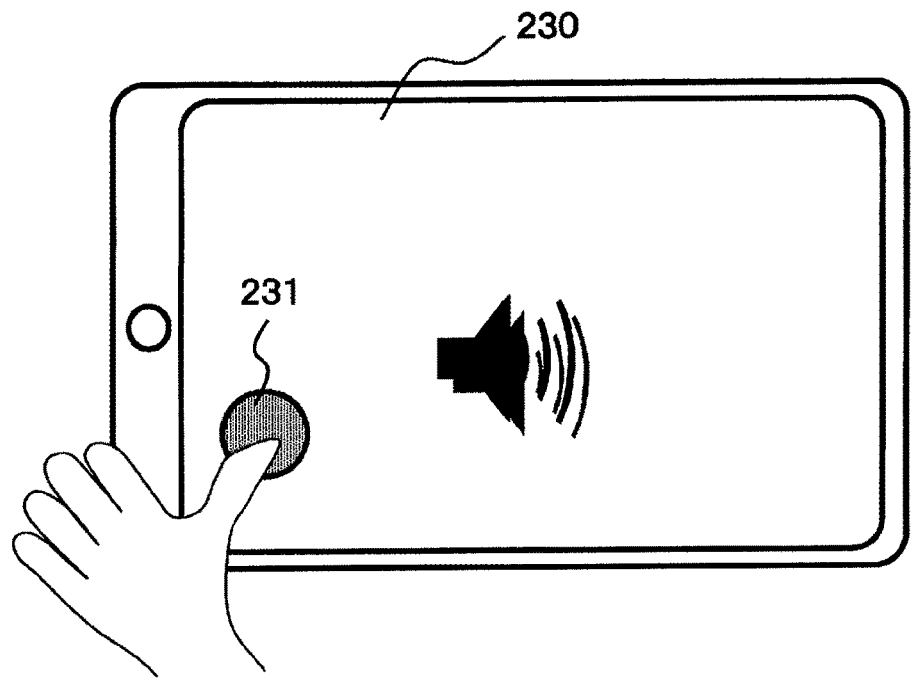
FIG. 10 shows a diagram illustrating an example of an auditory stimulus-based one hand rhythm touch task instruction screen presented on a body movement presenting device.

FIG. 10 is a diagram illustrating an example of an auditory stimulus-based one hand rhythm touch task instruction screen 230 presented on the body movement presenting device 2.

If an auditory stimulus-based one hand rhythm touch task is selected via the body movement task selection screen 120 (refer to FIG. 3), the instruction data presenting unit 13 of the body movement instruction unit 10 (refer to FIG. 1) displays the one hand rhythm touch task instruction screen 230 as illustrated in FIG. 10, on the body movement presenting device 2. At this time, a circular graphic 231 to be touched by a subject is displayed on the one hand rhythm touch task instruction screen 230.

Subsequently, the instruction data presenting unit 13 repetitively outputs, from a loudspeaker, touch instruction sound for instructing a timing at which the subject is to perform a touch operation, at a specific time interval or at a random time interval. The subject touches the above-described circular graphic 231 with, for example, a thumb, at a timing synchronized as far as possible with a timing at which the touch instruction sound is output.

In addition, in many cases, a subject is at an old age, touch instruction sound for auditory stimulus is preferably large sound, and sound other than high tone sound (the same applies to the descriptions of FIGS. 11 and 12 to be given later).

By using data on the body movement (hand and finger movement) of the subject that has been obtained through the auditory stimulus-based one hand rhythm touch task, the cognitive impairment degree S can be calculated as described later. In addition, in this one hand rhythm touch task, when the touch instruction sound is output at an equal time interval, the cognitive impairment degree S that is based on a predictive capability of the subject with respect to the auditory stimulus can be evaluated. In addition, when the touch instruction sound is output at a random time interval, the cognitive impairment degree S that is based on the response speed of the subject with respect to the auditory stimulus can be evaluated.

In addition, the effects of this one hand rhythm touch task are similar to those in other rhythm touch tasks to be described below.

In the example illustrated in FIG. 10, the circular graphic 231 to be touched by the subject is displayed on the left side on the one hand rhythm touch task instruction screen 230, and is touched by the left thumb of the subject. Alternatively, the circular graphic 231 to be touched by the subject may be displayed on the right side on the one hand rhythm touch task instruction screen 230, and may be touched by a right thumb of the subject.

Figure 11:
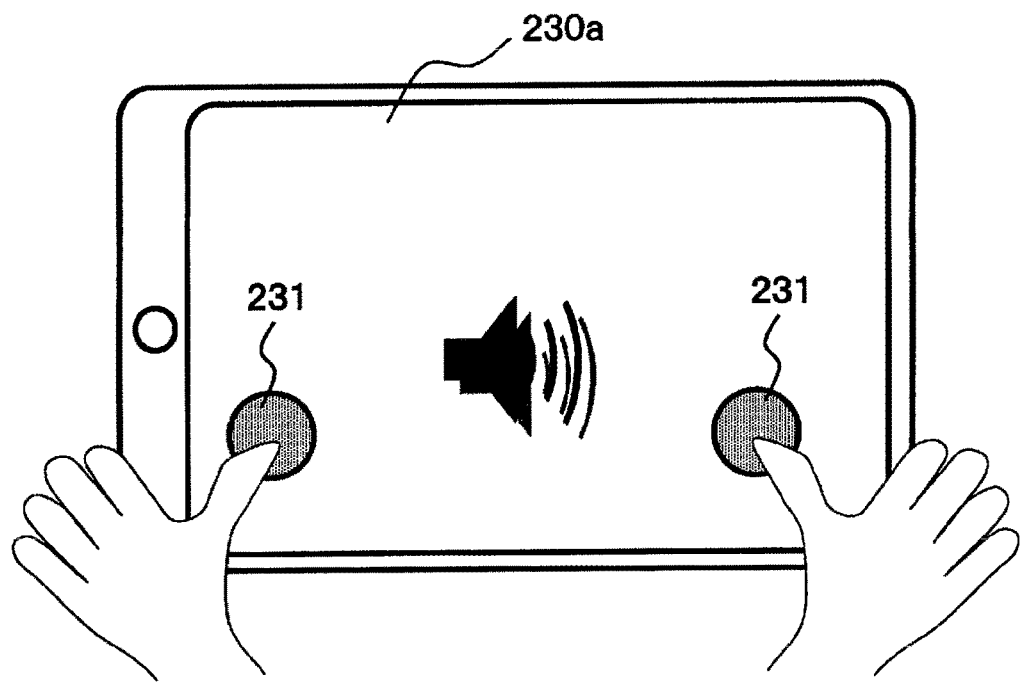
FIG. 11 shows a diagram illustrating an example of an auditory stimulus-based both hand rhythm touch task instruction screen presented on a body movement presenting device.

FIG. 11 is a diagram illustrating an example of an auditory stimulus-based both hand rhythm touch task instruction screen 230a presented on the body movement presenting device 2.

If an auditory stimulus-based both hand rhythm touch task is selected via the body movement task selection screen 120 (refer to FIG. 3), the instruction data presenting unit 13 displays the both hand rhythm touch task instruction screen 230a as illustrated in FIG. 11, on the body movement presenting device 2. At this time, two circular graphics 231 to be respectively touched by the right hand and the left hand of the subject are displayed on the both hand rhythm touch task instruction screen 230a.

Subsequently, the instruction data presenting unit 13 repetitively outputs, from a loudspeaker, touch instruction sound for instructing a timing at which the subject is to perform a touch operation, at a specific time interval or at a random time interval. The subject simultaneously touches the respective two circular graphics 231 with, for example, a left thumb and a right thumb, at a timing synchronized as far as possible with a timing at which the touch instruction sound is output.

Figure 12:
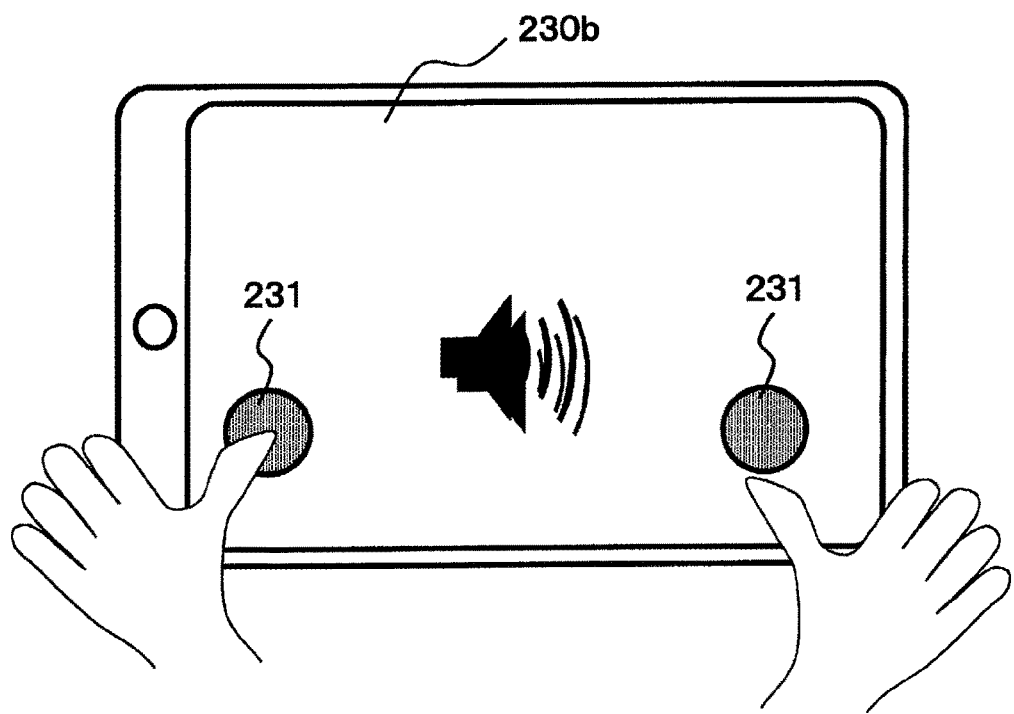
FIG. 12 shows a diagram illustrating an example of an auditory stimulus-based both hand alternate rhythm touch task instruction screen presented on a body movement presenting device.

FIG. 12 is a diagram illustrating an example of an auditory stimulus-based both hand alternate rhythm touch task instruction screen 230b presented on the body movement presenting device 2.

If a both hand alternate rhythm touch task is selected via the body movement task selection screen 120 (refer to FIG. 3), the instruction data presenting unit 13 displays the both hand alternate rhythm touch task instruction screen 230b as illustrated in FIG. 12, on the body movement presenting device 2. At this time, two circular graphics 231 to be respectively touched by the right hand and the left hand of the subject are displayed on the both hand alternate rhythm touch task instruction screen 230b.

Subsequently, the instruction data presenting unit 13 repetitively outputs, from a loudspeaker, touch instruction sound for instructing a timing at which the subject is to perform a touch operation, at a specific time interval or at a random time interval. The subject alternately touches the two circular graphics 231 with, for example, the left thumb or the right thumb, at a timing synchronized as far as possible with a timing at which the touch instruction sound is output.

In addition, in the both hand alternate rhythm touch task, different types of touch instruction sound may be output according to the left and right circular graphics 231 to be touched. For example, different pitches of touch instruction sound may be output between the left and right circular graphics 231, or touch instruction sound of different musical instruments may be output between the left and right circular graphics 231.

(b. Visual Stimulus-Based Rhythm Touch Task)

Figure 13:
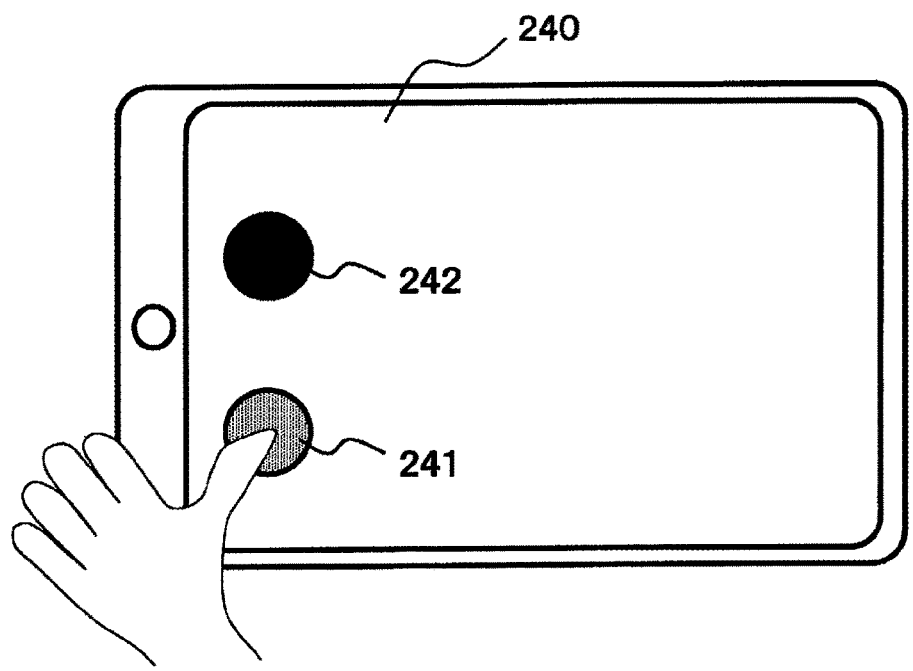
FIG. 13 shows a diagram illustrating an example of a visual stimulus-based one hand rhythm touch task instruction screen presented on a body movement presenting device.

FIG. 13 is a diagram illustrating an example of a visual stimulus-based one hand rhythm touch task instruction screen 240 presented on the body movement presenting device 2. If a visual stimulus-based one hand rhythm touch task is selected via the body movement task selection screen 120 (refer to FIG. 3), the instruction data presenting unit 13 displays the one hand rhythm touch task instruction screen 240 as illustrated in FIG. 13, on the body movement presenting device 2. At this time, a circular graphic 241 to be touched by a subject is displayed on the one hand rhythm touch task instruction screen 240.

Subsequently, the instruction data presenting unit 13 repetitively displays (but deletes immediately after displaying) a touch instruction graphic 242 for instructing a timing at which the subject is to perform a touch operation, at a specific time interval or at a random time interval. The subject touches the circular graphic 241 at a timing synchronized as far as possible with a timing at which the touch instruction graphic 242 is displayed.

In addition, the touch instruction graphic 242 for visual stimulus is not limited to the black filled circle. Since the subject is at an old age in many cases, the touch instruction graphic 242 preferably has an eye-catching configuration including a bright primary color rather than the black filled circle (the same applies to the descriptions of FIGS. 14 and 15).

Figure 14:
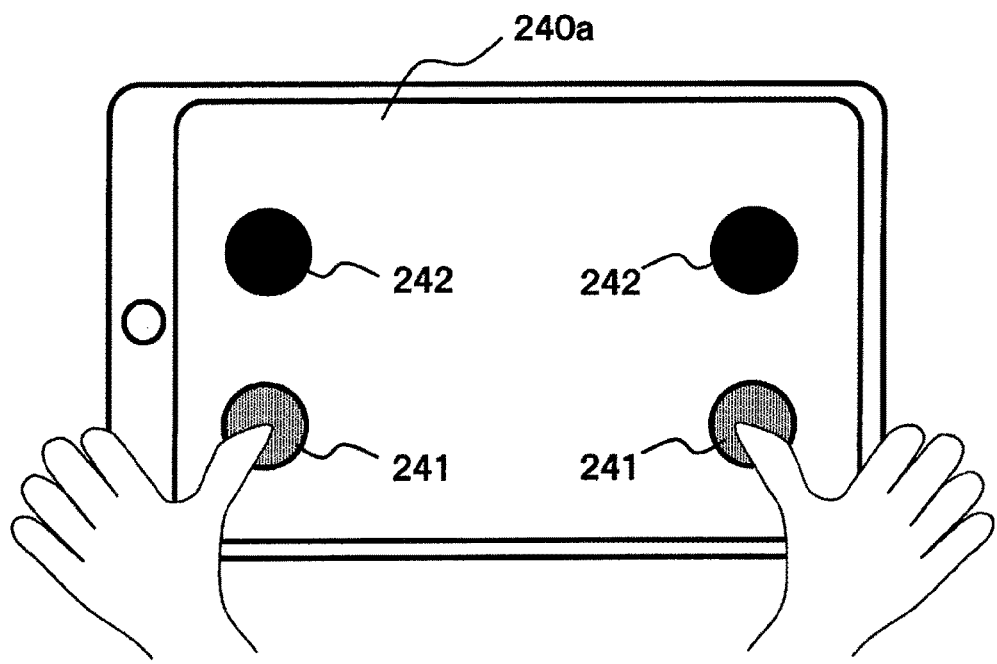
FIG. 14 shows a diagram illustrating an example of a visual stimulus-based both hand rhythm touch task instruction screen presented on a body movement presenting device.

FIG. 14 is a diagram illustrating an example of a visual stimulus-based both hand rhythm touch task instruction screen 240a presented on the body movement presenting device 2.

If a visual stimulus-based both hand rhythm touch task is selected via the body movement task selection screen 120 (refer to FIG. 3), the instruction data presenting unit 13 displays the both hand rhythm touch task instruction screen 240a as illustrated in FIG. 14, on the body movement presenting device 2. At this time, two circular graphics 241 to be respectively touched by the right hand and the left hand of the subject are displayed on the both hand rhythm touch task instruction screen 240a.

Subsequently, the instruction data presenting unit 13 repetitively displays (but deletes immediately after displaying) touch instruction graphics 242 for instructing a timing at which the subject is to perform a touch operation, at a specific time interval or at a random time interval. The subject simultaneously touches the respective two circular graphics 241 with, for example, the left thumb and the right thumb, at a timing synchronized as far as possible with a timing at which the touch instruction graphics 242 are displayed.

Figure 15:
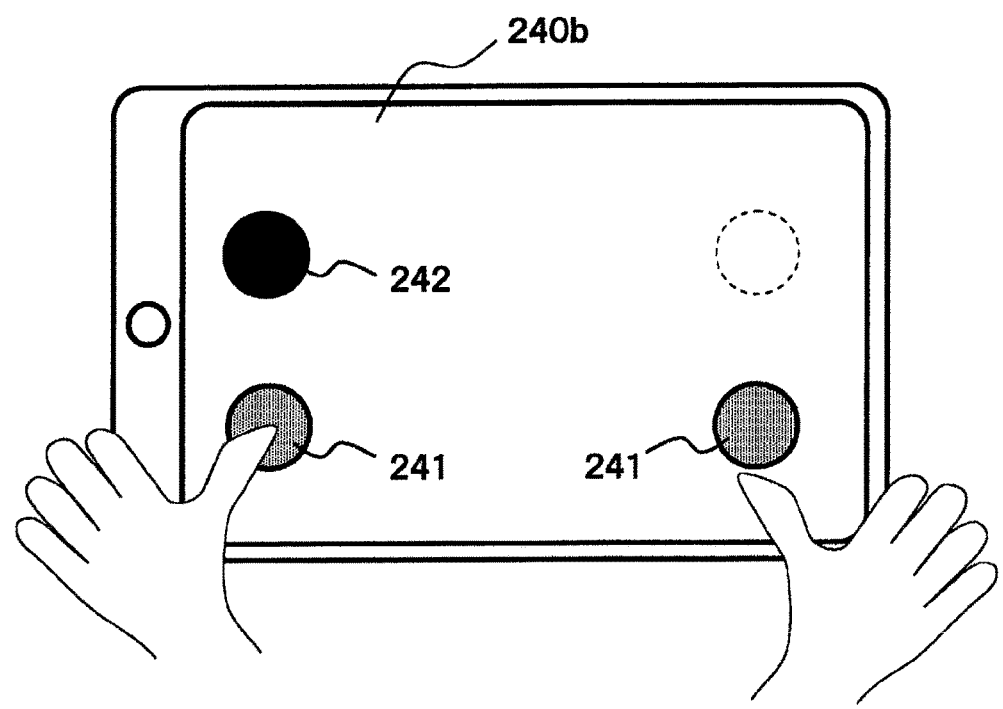
FIG. 15 shows a diagram illustrating an example of a visual stimulus-based both hand alternate rhythm touch task instruction screen presented on a body movement presenting device.

FIG. 15 is a diagram illustrating an example of a visual stimulus-based both hand alternate rhythm touch task instruction screen 240b presented on the body movement presenting device 2.

If a visual stimulus-based both hand alternate rhythm touch task is selected via the body movement task selection screen 120 (refer to FIG. 3), the instruction data presenting unit 13 displays the both hand alternate rhythm touch task instruction screen 240b as illustrated in FIG. 15, on the body movement presenting device 2. At this time, two circular graphics 241 to be respectively touched by the right hand and the left hand of the subject are displayed on the both hand alternate rhythm touch task instruction screen 240b.

Subsequently, the instruction data presenting unit 13 repetitively displays (but deletes immediately after displaying) a touch instruction graphic 242 for instructing a timing at which the subject is to perform a touch operation, at a specific time interval or at a random time interval. The subject alternately touches the two circular graphics 241 with, for example, the left thumb or the right thumb, at a timing synchronized as far as possible with a timing at which the touch instruction graphic 242 is displayed.

(c. Metronome-Type Rhythm Touch Task)

Figure 16:
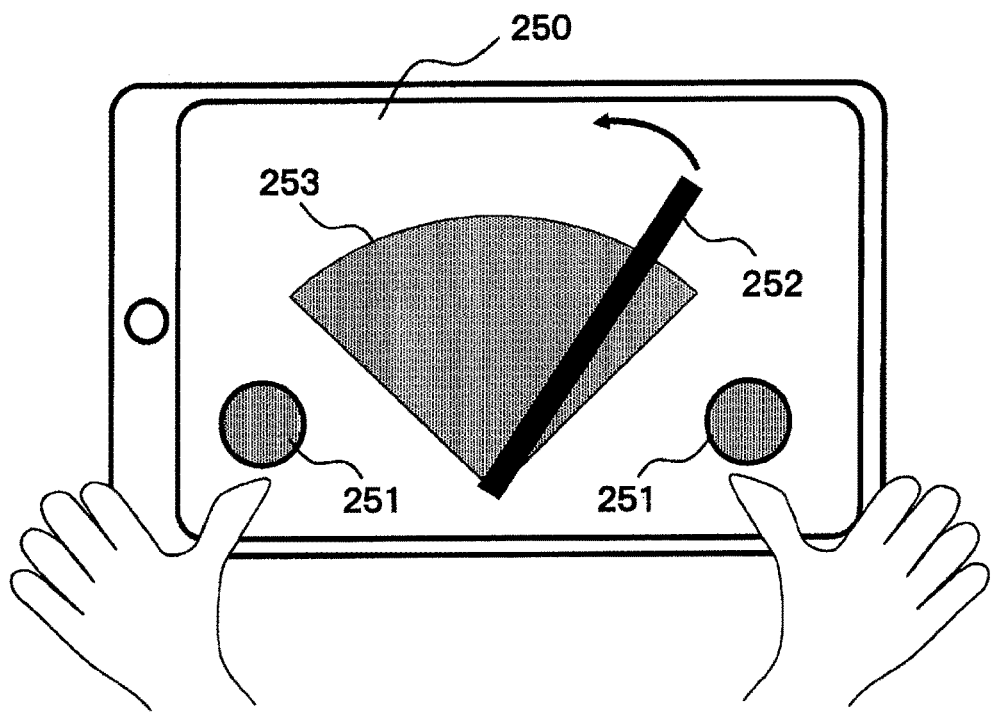
FIG. 16 shows a diagram illustrating an example of a metronome-type rhythm touch task instruction screen presented on a body movement presenting device.

FIG. 16 is a diagram illustrating an example of a metronome-type rhythm touch task instruction screen 250 presented on the body movement presenting device 2.

If a metronome-type rhythm touch task is selected via the body movement task selection screen 120 (refer to FIG. 3), the instruction data presenting unit 13 displays the metronome-type rhythm touch task instruction screen 250 as illustrated in FIG. 16, on the body movement presenting device 2. At this time, two circular graphics 251 to be respectively touched by the right hand and the left hand of the subject are displayed on the metronome-type rhythm touch task instruction screen 250. Furthermore, a pendulum 252 for a metronome and a fan-shaped graphic 253 representing the amplitude range of the pendulum 252 are displayed on the metronome-type rhythm touch task instruction screen 250.

The pendulum 252 swings in the range of the fan-shaped graphic 253 at a fixed cycle. Thus, the subject touches with the right thumb the circular graphic 251 on the right side at a timing synchronized with a timing at which the pendulum 252 reaches the right end of the fan-shaped graphic 253. The subject touches with the left thumb the circular graphic 251 on the left side at a timing synchronized with a timing at which the pendulum 252 reaches the left end of the fan-shaped graphic 253.

Thus, the metronome-type rhythm touch task can be said to be a substantially similar body movement task to the visual stimulus-based both hand alternate rhythm touch task illustrated in FIG. 15. In the case of the metronome-type rhythm touch task, however, since the subject can observe and predict the motion of the pendulum 252, the cognitive impairment degree S including a predictive capability of the subject can be evaluated.

In addition, in the metronome-type rhythm touch task, the subject alternately touches the circular graphics 251 with both hands. If this configuration is changed so that the subject performs a touch operation with one hand, or simultaneously performs a touch operation with both hands, the metronome-type rhythm touch task can be regarded as a substantially similar body movement task to the one hand rhythm touch task or the both hand rhythm touch task.

(Calculation of Positional Accuracy, Time-Series Accuracy, and Cognitive Impairment Degree)

In each rhythm touch task described above, the instruction and detection data comparing unit 31 (refer to FIG. 1) determines whether a touch position coordinate (X, Y) touched by the subject that is obtained by the detection data acquisition unit 21 is included in the circular graphic 231, 241, or 251 displayed prior to the touch.

Then, if the touch position coordinate (X, Y) touched by the subject is included in the circular graphic 231, 241, or 251, the positional accuracy calculation unit 32 determines that the touch has succeeded. If not, the positional accuracy calculation unit 32 determines that the touch has failed, and calculates a touch failure rate. The positional accuracy calculation unit 32 then defines the calculated touch failure rate as the positional accuracy $m_d$. In other words, the calculation is performed as follows: the positional accuracy $m_d$=touch failure times/(touch success times+touch failure times).

In addition, it seems a bit strange to use the touch failure rate as the positional accuracy $m_d$ rather than the touch success rate. This is because this specification defines that a positional accuracy $m_d$ smaller in value means higher accuracy.

For example, when one rhythm touch task includes 20 visual stimuli or auditory stimuli, and if a subject fails five times in touching the circular graphic 231, 241, or 251 to be touched, the positional accuracy $m_d$ in this case is 0.25.

In addition, the time-series accuracy $m_T$ is calculated in a similar manner to that in the case of the above-described reaching task. More specifically, the time-series accuracy calculation unit 33 calculates an average value ($=\Sigma T_i/N$: N is the number of times visual stimulus or auditory stimulus is presented) of touch delay times $T_i$, each of which is a difference between a time $\tau_i$ when visual stimulus or auditory stimulus is presented and a time $t_i$ when the subject performs a touch operation, and defines the calculated average value of the touch delay times $T_i$ as the time-series accuracy $m_T$.

If the positional accuracy $m_d$ and the time-series accuracy $m_T$ are obtained in the above-described manner, the cognitive impairment degree calculation unit 41 can calculate the cognitive impairment degree S in a similar manner to that described in the above embodiment. In addition, the cognitive impairment degree output unit 42 can output the calculated cognitive impairment degree S and the chronological change graph (refer to FIG. 9) of the cognitive impairment degree S, to the output device 5 such as a liquid crystal display device and a printer.

In other words, by executing a rhythm touch task, the subject or the helper of the subject can easily evaluate the degree (the cognitive impairment degree S) of a cognitive function decline including cerebral dysfunction of the subject.

3.2 Finger Opening and Closing Tap Task

Figure 17:
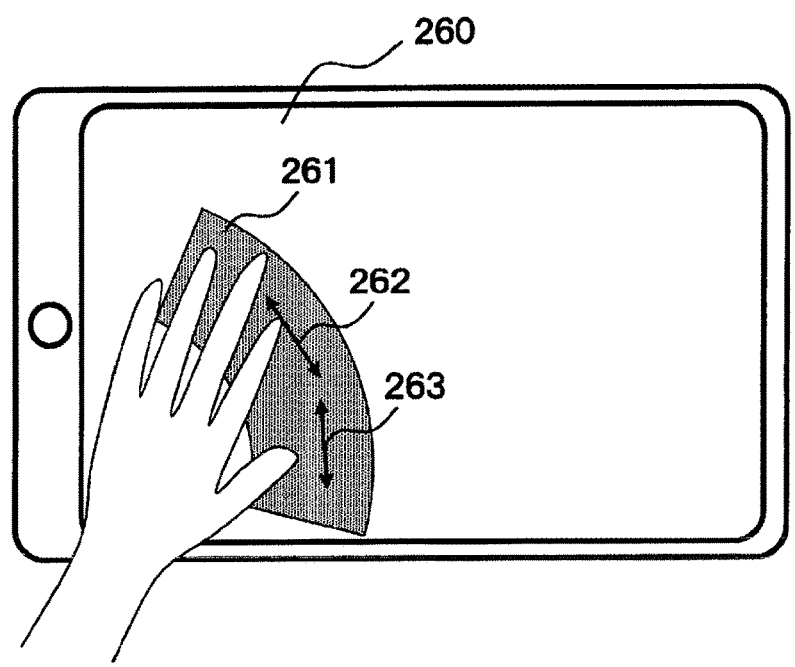
FIG. 17 shows a diagram illustrating an example of a one hand finger opening and closing tap task instruction screen presented on a body movement presenting device.

FIG. 17 is a diagram illustrating an example of a one hand finger opening and closing tap task instruction screen 260 presented on the body movement presenting device 2.

If a one hand finger opening and closing tap task is selected via the body movement task selection screen 120 (refer to FIG. 3), the instruction data presenting unit 13 of the body movement instruction unit 10 (refer to FIG. 1) displays the one hand finger opening and closing tap task instruction screen 260 as illustrated in FIG. 17, on the body movement presenting device 2. Here, the one hand finger opening and closing tap task refers to a body movement task of a repetitive opening and closing movement of two fingers (e.g., a thumb and an index finger) of one hand of a subject.

Thus, a fan-shaped opening and closing designation region 261 for designating a region where the subject performs a two-finger opening and closing movement is displayed on the one hand finger opening and closing tap task instruction screen 260. In addition, the shape of the opening and closing designation region 261 is not limited to a fan shape. The opening and closing designation region 261 may have any shape as long as a resultant region can facilitate the two-finger opening and closing movement.

In the one hand finger opening and closing tap task, the subject repeats the opening and closing movement as largely and fast as possible in a state in which the thumb and the index finger, for example, are in contact with the fan-shaped graphic 261. At this time, the detection data acquisition unit 21 detects a coordinate value of a position touched by the thumb and a coordinate value of a position touched by the index finger, and calculates a distance between the touch positions of these two fingers as a distance L between two fingers. In addition, in FIG. 17, a both end arrow 262 indicates the opening and closing amplitude of the index finger, and a both end arrow 263 indicates the opening and closing amplitude of the thumb.

Figure 18:
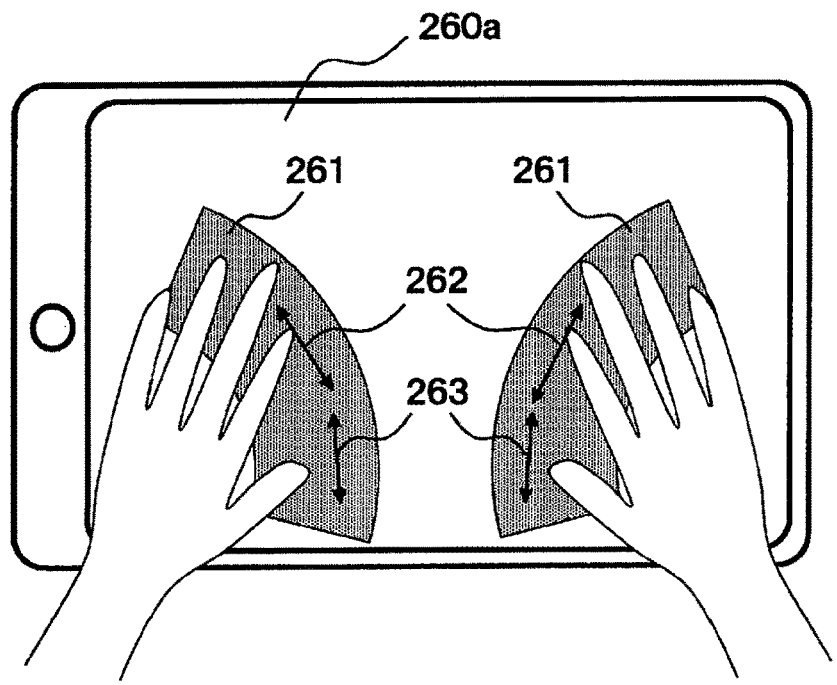
FIG. 18 shows a diagram illustrating an example of a both hand finger opening and closing tap task instruction screen presented on a body movement presenting device.
Figure 19:
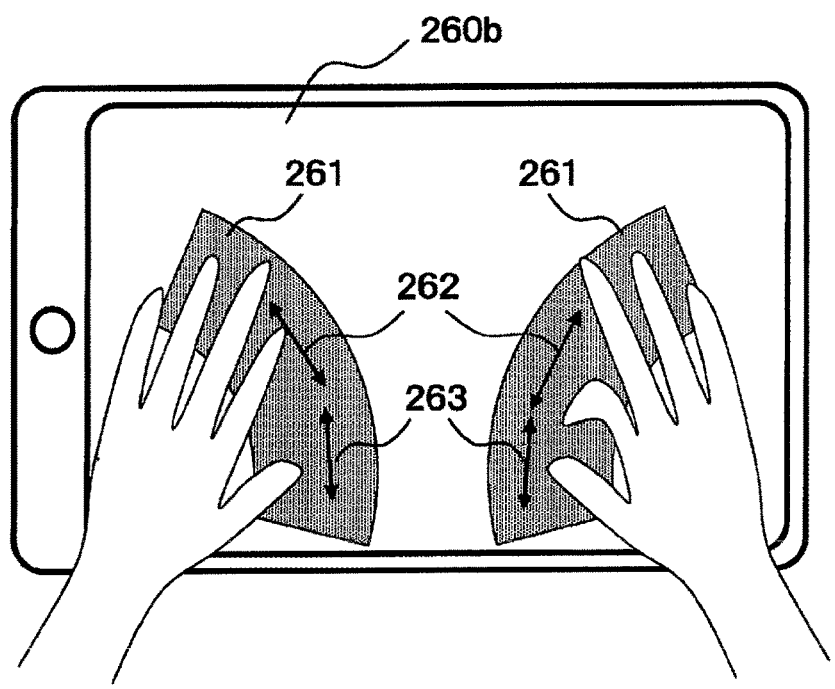
FIG. 19 shows a diagram illustrating an example of a both hand alternate finger opening and closing tap task instruction screen presented on a body movement presenting device.

Aside from the example illustrated in FIG. 17, finger opening and closing tap tasks include a both hand finger opening and closing tap task and a both hand alternate finger opening and closing tap task. FIG. 18 is a diagram illustrating an example of a both hand finger opening and closing tap task instruction screen 260a presented on the body movement presenting device 2. FIG. 19 is a diagram illustrating an example of a both hand alternate finger opening and closing tap task instruction screen 260b. As illustrated in FIGS. 18 and 19, in the finger opening and closing tap tasks using both hands, two opening and closing designation regions 261 for the subject performing a two-finger opening and closing movement with both hands are displayed on each of the both hand finger opening and closing tap task instruction screen 260a and the both hand alternate finger opening and closing tap task instruction screen 260b.

The both hand finger opening and closing tap task and the both hand alternate finger opening and closing tap task are the same in that the subject performs a two-finger opening and closing movement using both hands. On the other hand, they are different from each other in that, while the two-finger opening and closing movement is simultaneously performed with both hands in the both hand finger opening and closing tap task, the two-finger opening and closing movement is alternately performed with one hand at a time in the both hand alternate finger opening and closing tap task.

In addition, in the finger opening and closing tap tasks described above with reference to FIGS. 17 to 19, the two-finger opening and closing movement is assumed to be performed without a time restriction being specifically imposed. Nevertheless, visual stimulus or auditory stimulus to the subject may be generated as in the case of the rhythm touch task, and the two finger opening and closing movement may be performed in accordance with the generated stimulus.

(Calculation of Positional Accuracy, Time-Series Accuracy, and Cognitive Impairment Degree)

Figure 20:
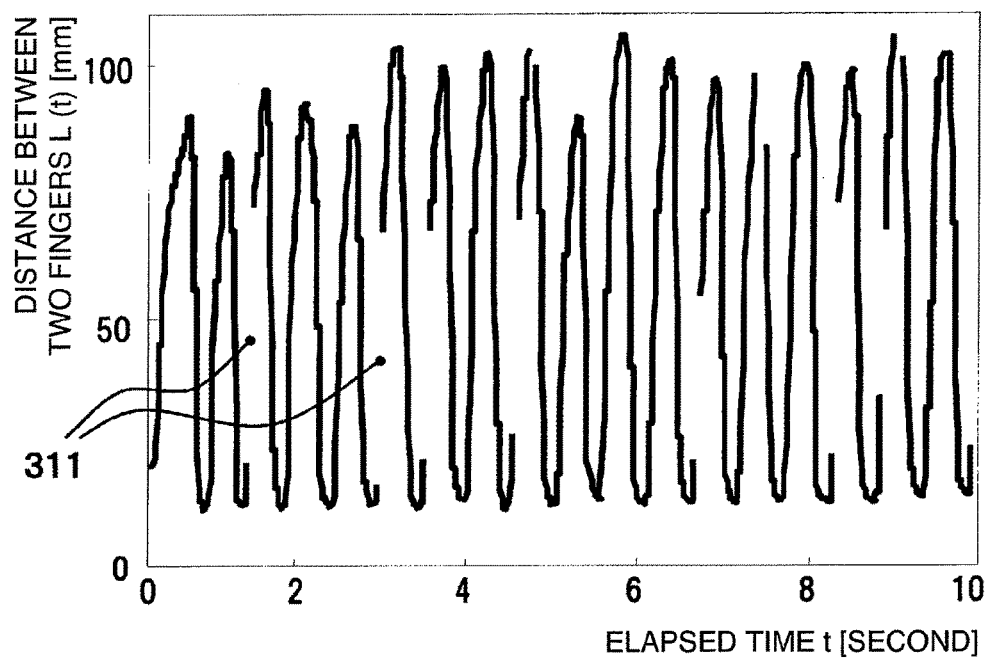
FIG. 20 shows a diagram illustrating an example of a temporal transitional graph of a distance L (t) between two fingers that is created in a case in which a finger opening and closing tap task is performed.

FIG. 20 is a diagram illustrating an example of a temporal transitional graph of a distance L (t) between two fingers that is created in a case in which a finger opening and closing tap task is performed.

When the finger opening and closing tap tasks described with reference to FIGS. 17 to 19 are performed, the instruction and detection data comparing unit 31 (refer to FIG. 1) creates the temporal transitional graph of the distance L (t) between two fingers as illustrated in FIG. 20, using the distance L (t) between two fingers that is acquired by the detection data acquisition unit 21 at every 10 milliseconds, for example. In addition, in the graph illustrated in FIG. 20, a horizontal axis indicates an elapsed time from the start of the finger opening and closing tap task, and a vertical axis indicates a distance L (t) between two fingers that is obtained at an elapsed time t.

In addition, in the finger opening and closing tap task, the opening and closing movement is assumed to be performed in a state in which two fingers are constantly in touch with the screen (touch panel). In actual situations, either one or both of the fingers may be detached from the screen when the two-finger opening and closing movement is being performed. In such a case, lost parts 311 are generated among acquired distances L (t) between two fingers. In many cases, however, the lost parts 311 can be interpolated using a general interpolation method such as spline interpolation.

Next, the positional accuracy calculation unit 32 calculates, from the temporal transitional graph of the distance L (t) between two fingers that is illustrated in FIG. 20, an amplitude $A_i$ of every one two-finger opening and closing movement (a difference between the maximum value and the minimum value of the distance L (t) that are obtained for every one finger opening and closing movement). The positional accuracy calculation unit 32 further calculates a standard deviation of amplitudes A. The positional accuracy calculation unit 32 then defines the calculated standard deviation of the amplitudes $A_i$ as the positional accuracy $m_d$.

In addition, the time-series accuracy calculation unit 33 calculates, from the temporal transitional graph of the distance L (t) between two fingers that is illustrated in FIG. 20, a time interval $t_i$ of every one two-finger opening and closing movement (a time from when the maximum value or the minimum value of the distance L (t) is obtained through the finger opening and closing movement to when the next maximum value or the minimum value is obtained). The time-series accuracy calculation unit 33 further calculates the standard deviation of time intervals $t_i$. The time-series accuracy calculation unit 33 then defines the calculated standard deviation of the time intervals t, as the time-series accuracy $m_T$.

If the positional accuracy $m_d$ and the time-series accuracy $m_T$ are obtained in the above-described manner, the cognitive impairment degree calculation unit 41 can calculate the cognitive impairment degree S in a similar manner to that described in the above embodiment. In addition, the cognitive impairment degree output unit 42 can output the calculated cognitive impairment degree S and the chronological change graph (refer to FIG. 9) of the cognitive impairment degree S, to the output device 5 such as a liquid crystal display device and a printer.

In other words, by executing a finger opening and closing tap task, the subject or the helper of the subject can easily evaluate the degree (the cognitive impairment degree S) of a cognitive function decline including cerebral dysfunction of the subject.

3.3 Five Finger Touch Task

Figure 21:
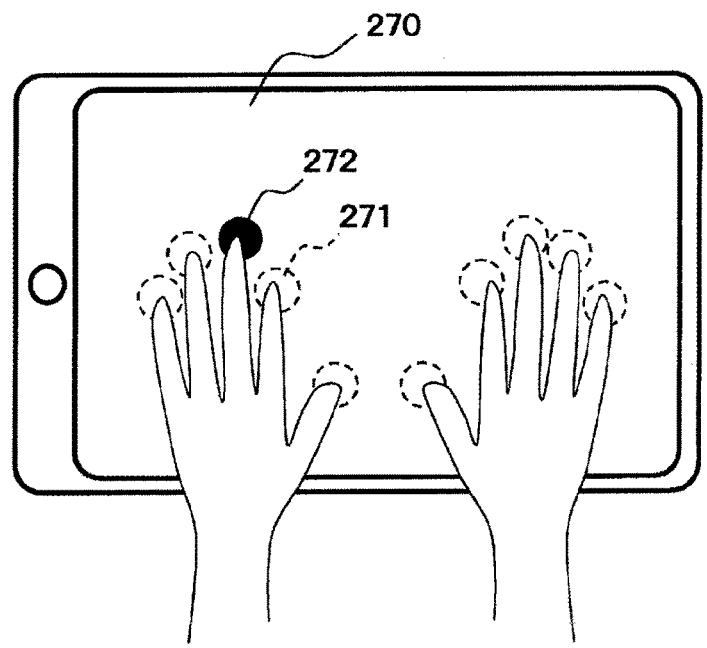
FIG. 21 shows a diagram illustrating an example of a five finger touch task instruction screen presented on a body movement presenting device.

FIG. 21 is a diagram illustrating an example of a five finger touch task instruction screen 270 presented on the body movement presenting device 2.

If a five finger touch task is selected via the body movement task selection screen 120 (refer to FIG. 3), the instruction data presenting unit 13 of the body movement instruction unit 10 (refer to FIG. 1) displays the five finger touch task instruction screen 270 as illustrated in FIG. 21, on the body movement presenting device 2. At this time, ten touch instruction regions 271 respectively corresponding to left five fingers and right five fingers are displayed on the five finger touch task instruction screen 270 as broken-line circles, for example.

Next, the instruction data presenting unit 13 selects one from the ten touch instruction regions 271, and displays a touch instruction graphic 272 at the position of the selected touch instruction region 271. In response to this, the subject touches the displayed touch instruction graphic 272 or the touch instruction region 271 at the position. In addition, when the touch instruction graphic 272 is touched by the subject, or when a predetermined time elapses, the instruction data presenting unit 13 deletes the touch instruction graphic 272 that has been displayed so far. Furthermore, the instruction data presenting unit 13 selects another touch instruction region 271, and newly displays a touch instruction graphic 272 at the selected touch instruction region 271.

Then, the instruction data presenting unit 13 repeats a predetermined number of times the above-described operation of selecting one of the touch instruction regions 271, displaying the touch instruction graphic 272 at the position of the selected touch instruction region 271, and detecting a touch operation performed by the subject. At this time, the touch instruction regions 271 may be selected according to a predetermined order such as, for example, an arrangement order of fingers (e.g., left little finger→left annular finger→left middle finger→left index finger→left thumb→right little finger→right annular finger→right middle finger→right index finger→right thumb), or may be selected according to a random order.

In addition, the touch instruction regions 271 may be provided at positions roughly corresponding to five fingers of the subject, and the positions may be calibrated according to each subject. When the positions are calibrated, the subject is prompted to touch the display screen (touch panel) with five fingers of each hand. The touch instruction regions 271 corresponding to respective fingers of both hands (five fingers of each hand) are then set based on the respective positions touched at that time by the fingers of both hands (five fingers of each hand).

In addition, the shape of the touch instruction graphic 272 is not limited to the circle as illustrated in FIG. 21. The touch instruction graphic 272 may have other shapes as long as touch operations performed by five fingers of each hand can be separately detected.

(Calculation of Positional Accuracy, Time-Series Accuracy, and Cognitive Impairment Degree)

In the above described five finger touch task, the positional accuracy $m_d$ is obtained by calculating a touch failure rate in a similar manner to that in the case of the above-described rhythm touch task.

In other words, every time the touch instruction graphic 272 is displayed, the instruction and detection data comparing unit 31 (refer to FIG. 1) acquires a touch position coordinate (X, Y) touched by the subject in response to the touch instruction graphic 272 being displayed. Then, if the acquired touch position coordinate (X, Y) is included in the touch instruction graphic 272 displayed prior to the touch operation, or the touch instruction region 271 at the position, the positional accuracy calculation unit 32 determines that the touch has succeeded. If not, the positional accuracy calculation unit 32 determines that the touch has failed. The positional accuracy calculation unit 32 then calculates a touch failure rate (=touch failure times/touch success times+ touch failure times), and defines the calculated touch failure rate as the positional accuracy $m_d$.

In addition, as described above, the reason why the touch failure rate is used as the positional accuracy $m_d$ rather than the touch success rate lies in that this specification defines that a positional accuracy $m_d$ smaller in value means higher accuracy.

In addition, the time-series accuracy $m_T$ is calculated in a similar manner to that in the case of the above-described reaching task. More specifically, the time-series accuracy calculation unit 33 calculates an average value (=$\Sigma T_i/N$: N is the number of times the touch instruction graphic 272 is displayed) of touch delay times $T_i$, each of which is a difference between a time $\tau_i$ when the touch instruction graphic 272 is displayed and a time $t_i$ when the subject touches the touch instruction graphic 272 or the touch instruction regions 271 at the position, and defines the calculated average value of the touch delay times $T_i$ as the time-series accuracy $m_T$.

If the positional accuracy $m_d$ and the time-series accuracy $m_T$ are obtained in the above-described manner, the cognitive impairment degree calculation unit 41 can calculate the cognitive impairment degree S in a similar manner to that described in the above embodiment. In addition, the cognitive impairment degree output unit 42 can output the calculated cognitive impairment degree S and the chronological change graph (refer to FIG. 9) of the cognitive impairment degree S, to the output device 5 such as a liquid crystal display device and a printer.

In other words, by executing the five finger touch task, the subject or the helper of the subject can easily evaluate the degree (the cognitive impairment degree S) of a cognitive function decline including cerebral dysfunction of the subject.

(Usage Example of Five Finger Touch Task)

Figure 22:
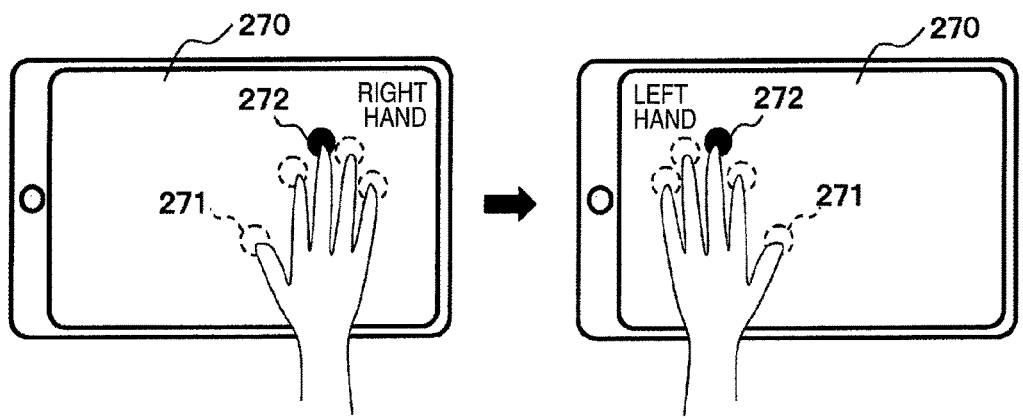
FIG. 22 shows a diagram illustrating a usage example of a five finger touch task.

FIG. 22 is a diagram illustrating a usage example of a five finger touch task. As illustrated in FIG. 22, the instruction data presenting unit 13 initially selects, for the right hand, the touch instruction regions 271 according to a specific order, and sequentially displays the touch instruction graphics 272. The instruction data presenting unit 13 further selects, for the left hand, the touch instruction regions 271 according to the same order as that in the case of the right hand, and sequentially displays the touch instruction graphics 272. For example, if the touch instruction graphics 272 are sequentially displayed in the following order: little finger→middle finger→thumb→index finger→annular finger→ . . . as for the left finger, the touch instruction graphics 272 are sequentially displayed in the same order (little finger→middle finger→thumb→index finger→annular finger→ . . . ) as for the right hand.

Thus, the subject initially touches, following the touch instruction graphics 272 displayed on the right side in a specific order, the displayed touch instruction graphics 272 or the touch instruction regions 271 at the positions with right hand fingers. The subject subsequently touches, following the touch instruction graphics 272 displayed on the left side in the same order, the displayed touch instruction graphics 272 or the touch instruction regions 271 at the positions with left hand fingers.

In such a five finger touch task, based on the cognitive impairment degree S obtained through the execution of the five finger touch task, it can be evaluated whether the effect of the movement learned by one hand also appears in the other hand. For example, it is generally believed that, if a cognitive function declines, a capability of copying a series of movement commands declines in left and right motor areas. If the five finger touch task is used in a manner as illustrated in FIG. 22, the five finger touch task can be used as a tool for verifying a general knowledge and a theory that are related to a cerebral function.

3.4 Tracking Task

Figure 23:
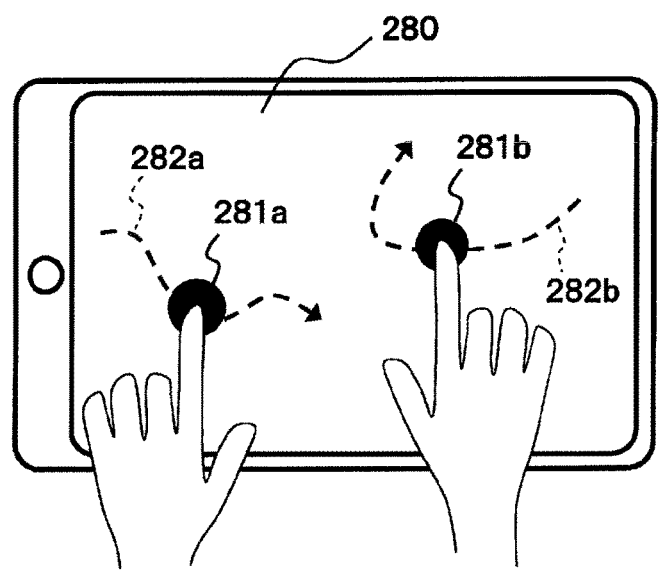
FIG. 23 shows a diagram illustrating an example of a tracking task instruction screen presented on a body movement presenting device.

FIG. 23 is a diagram illustrating an example of a tracking task instruction screen 280 presented on the body movement presenting device 2.

If a tracking task is selected via the body movement task selection screen 120 (refer to FIG. 3), the instruction data presenting unit 13 of the body movement instruction unit 10 (refer to FIG. 1) displays the tracking task instruction screen 280 as illustrated in FIG. 23, on the body movement presenting device 2. At this time, two tracking target graphics 281a and 281b for the left hand and the right hand, respectively, are displayed on the tracking task instruction screen 280.

Then, the instruction data presenting unit 13 moves the two tracking target graphics 281a and 281b on the tracking task instruction screen 280 so that the two tracking target graphics 281a and 281b draw trajectories 282a and 282b different from each other. With left and right fingers being kept in touch with the tracking task instruction screen 280, the subject tracks these two tracking target graphics 281a and 281b with the respective fingers in accordance with the movements of the tracking target graphics 281a and 281b. In addition, the two tracking target graphics 281a and 281b may be different from each other in display color or shape.

(Calculation of Positional Accuracy, Time-Series Accuracy, and Cognitive Impairment Degree)

When the tracking task is executed, the instruction and detection data comparing unit 31 (refer to FIG. 1) obtains a distance between a position coordinate $(X_{0j}(t), Y_{0j}(t))$ (j=L or R) to which the tracking target graphic 281a or 281b moves, and a touch position coordinate $(X_j(t), Y_j(t))$ (j=l or r) of the left or right finger of the subject, and the obtained distance is represented as $L_j(t)$ (j=l, r). Here, j=l means left, and j=r means right. In addition, $L_l(t)$ and $L_r(t)$ are referred to as a left hand error and a right hand error, respectively.

Subsequently, the positional accuracy calculation unit 32 calculates a time average of left hand errors $L_l(t)$ and a time average of right hand errors $L_r(t)$. Furthermore, the positional accuracy calculation unit 32 defines an average value of the calculated time average of the left hand errors $L_l$ (t) and the calculated time average of the right hand errors $L_r$ (t), as the positional accuracy $m_d$.

The processing performed by the time-series accuracy calculation unit 33 will be described with reference to FIGS. 24(a) and 24(b).

FIGS. 24(a) and 24(b) are diagrams illustrating a relationship between a position coordinate of a tracking target graphic and a touch position coordinate of a subject, as an example of a schematic temporal transitional change graph. FIG. 24(a) illustrates an example of a temporal transitional change of an X coordinate, and FIG. 24(b) illustrates an example of a temporal transitional change of a Y coordinate.

A broken line 351 in FIG. 24(a) indicates a temporal transitional change of an X coordinate of the tracking target graphic 281a (or 281b) on the left side (or right side) that is illustrated in FIG. 23, that is, $X_{0l}$ (t) (or $X_{0r}$ (t)). In addition, a solid line 352 indicates a temporal transitional change of an X coordinate $X_l$ (t) (or $X_r$ (t)) of a touch position coordinate touched by the left finger (or right finger) of the subject.

Similarly, a broken line 361 in FIG. 24(b) indicates a temporal transitional change of a Y coordinate of the tracking target graphic 281a (or 281b) on the left side (or right side) that is illustrated in FIG. 23, that is, $Y_{0l}$ (t) (or $Y_{0r}$ (t)). In addition, a solid line 362 indicates a temporal transitional change of a Y coordinate $Y_l$ (t) (or $Y_r$ (t)) of a touch position coordinate touched by the left finger (or right finger) of the subject.

The time-series accuracy calculation unit 33 calculates a mutual correlation function $FX_l(\tau)$ (or $FX_r(\tau)$) between a function $X_{0l}$ (t) (or $X_{0r}$ (t)) indicated by the X coordinate of the tracking target graphic 281a (or 281b) and a function $X_l$ (t) (or $X_r$ (t)) indicated by the X coordinate of the touch position coordinate touched by the left finger (or right finger) of the subject.

Similarly, the time-series accuracy calculation unit 33 calculates a mutual correlation function $FY_l(\tau)$ (or $FY_r(\tau)$) between a function $Y_{0l}$ (t) (or $Y_{0r}$ (t)) indicated by the Y coordinate of the tracking target graphic 281a (or 281b) and a function $Y_l$ (t) (or $Y_r$ (t)) indicated by the Y coordinate of the touch position coordinate touched by the left finger (or right finger) of the subject.

In addition, the mutual correlation function is a function often used in the case of evaluating, when one signal of two time-series signals is shifted by a time $\tau_i$, a correlation between the both signals.

Through the above processing, the time-series accuracy calculation unit 33 obtains the four mutual correlation functions $FX_l(\tau)$, $FX_r(\tau)$, $FY_l(\tau)$, and $FY_r(\tau)$. The time-series accuracy calculation unit 33 then calculates shift times $\tau_{Xl}$, $\tau_{Xr}$, $\tau_{Yl}$, and $\tau_{Yr}$ by which the respective mutual correlation functions $FX_l(\tau)$, $FX_r(\tau)$, $FY_l(\tau)$, and $FY_r(\tau)$ have the maximum values.

Here, the shift time $\tau_{Xl}$ by which the mutual correlation function $FX_l(\tau)$ has the maximum value means that, when one of the function $X_{0l}$ (t) indicated by the broken line 351 illustrated in FIG. 24(a) and the function $X_l$ (t) indicated by the solid line 352 illustrated in FIG. 24(a) is shifted by the $\tau_{Xl}$, the matching degree of both of the graphs becomes the highest.

Thus, the shift time $\tau_{Xl}$ obtained from the mutual correlation function $FX_1(\tau)$ is preferable as an index representing the time-series accuracy $m_T$. The similarly obtained shift times $\tau_{Xr}$, $\tau_{Yl}$, and $\tau_{Yr}$ are also preferable as an index representing the time-series accuracy $m_T$.

The time-series accuracy calculation unit 33 then averages the four shift times $\tau_{Xl}$, $\tau_{Xr}$, $\tau_{Yl}$, and $\tau_{Yr}$ calculated in the above-described manner, and defines the calculated average as the time-series accuracy $m_T$ in the tracking task.

If the positional accuracy $m_d$ and the time-series accuracy $m_T$ in the tracking task are obtained in the above-described manner, the cognitive impairment degree calculation unit 41 can calculate the cognitive impairment degree S in a similar manner to that described in the embodiment of the above-described reaching task. In addition, the cognitive impairment degree output unit 42 can output the calculated cognitive impairment degree S and the chronological change graph (refer to FIG. 9) of the cognitive impairment degree S, to the output device 5 such as a liquid crystal display device and a printer.

In other words, by executing the tracking task, the subject or the helper of the subject can easily evaluate the degree (the cognitive impairment degree S) of a cognitive function decline including cerebral dysfunction of the subject.

4. Modified Example of Embodiment

Figure 25:
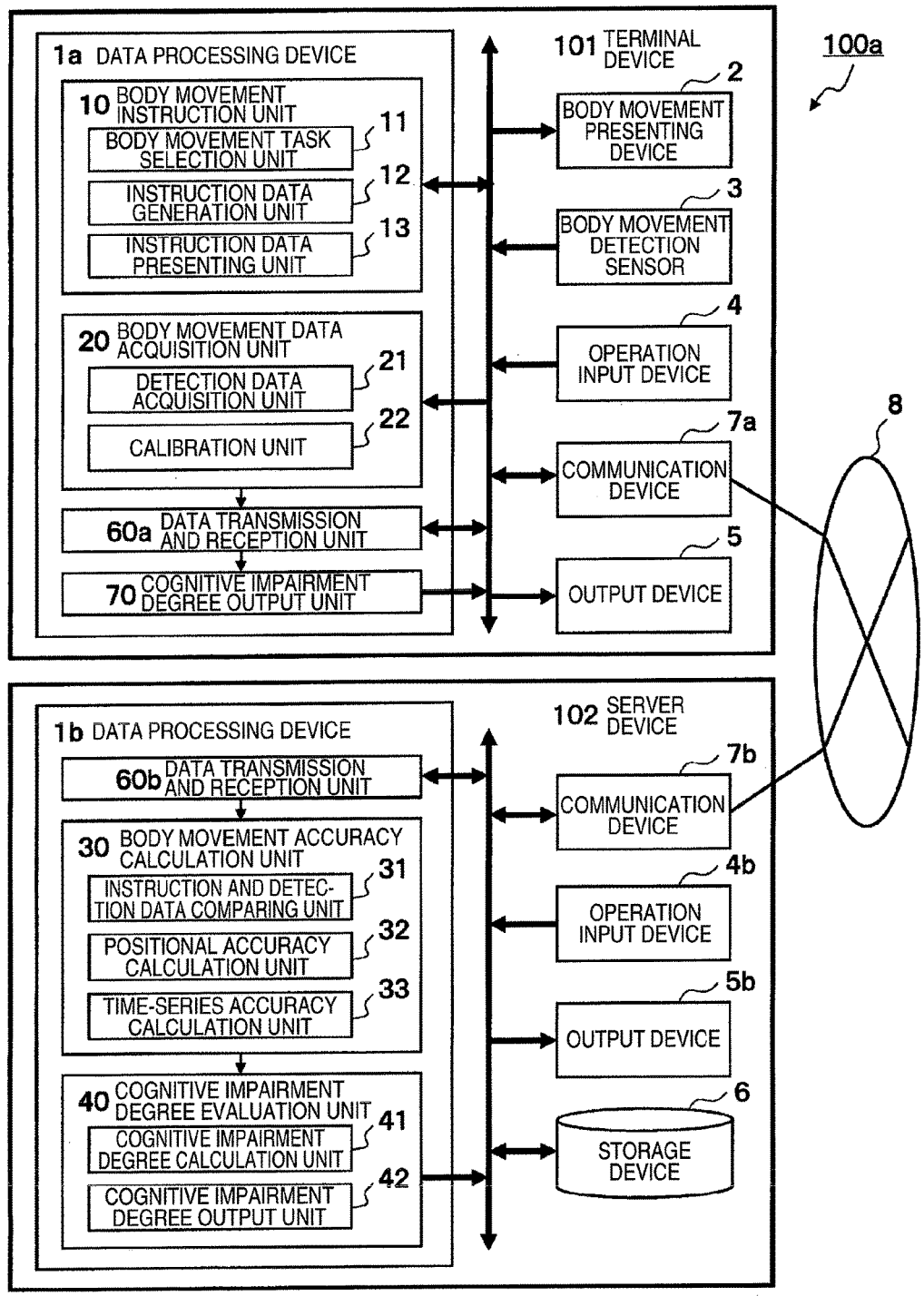
FIG. 25 shows a diagram illustrating an example of an entire configuration of a cerebral dysfunction evaluation apparatus according to a modified example of an embodiment of the present invention.

4.1 Modified Example of Configuration of Cerebral Dysfunction Evaluation Apparatus FIG. 25 is a diagram illustrating an example of an entire configuration of a cerebral dysfunction evaluation apparatus 100a according to a modified example of an embodiment of the present invention. The cerebral dysfunction evaluation apparatus 100a illustrated in FIG. 25 has functions approximately equivalent to those of the cerebral dysfunction evaluation apparatus 100 illustrated in FIG. 1. These functions are separately realized by a terminal device 101 and a server device 102 connected to each other by a communication network 8.

In the cerebral dysfunction evaluation apparatus 100a, the terminal device 101 has a function of presenting a body movement to a subject, and acquiring data of a body movement of the subject. In addition, the server device 102 has a function of receiving, via the communication network 8, the data of the body movement of the subject that has been acquired by the terminal device 101, and evaluating a cognitive impairment degree of the subject based on the received data of the body movement of the subject. Except for these points, the configuration and functions of the cerebral dysfunction evaluation apparatus 100a are the same as the configuration and functions of the cerebral dysfunction evaluation apparatus 100 illustrated in FIG. 1. Thus, hereinafter, only different parts will be mainly described.

The configuration of a data processing device 1a of the terminal device 101 is a configuration obtained by excluding the body movement accuracy calculation unit 30 and the cognitive impairment degree evaluation unit 40 from the data processing device 1 of the cerebral dysfunction evaluation apparatus 100 illustrated in FIG. 1, and adding a data transmission and reception unit 60a and a cognitive impairment degree output unit 70. Furthermore, the terminal device 101 is newly provided with a communication device 7a for connecting the data processing device 1a and the communication network 8.

The data transmission and reception unit 60a transmits detection data and calibration data of a body movement of the subject that have been acquired by the body movement data acquisition unit 20, to the server device 102 via the communication device 7a and the communication network 8. In addition, the data transmission and reception unit 60a receives data such as the cognitive impairment degree of the subject that has been evaluated by the server device 102. Then, the cognitive impairment degree output unit 70 outputs the data such as the cognitive impairment degree of the subject that has been evaluated by the server device 102 and received via the data transmission and reception unit 60a, to the output device 5.

In addition, the server device 102 includes a data processing device 1b, an operation input device 4b, an output device 5b, the storage device 6, a communication device 7b, and the like. The data processing device 1b includes the body movement accuracy calculation unit 30, the cognitive impairment degree evaluation unit 40, a data transmission and reception unit 60b, and the like. The data transmission and reception unit 60b receives the detection data and the calibration data of the body movement of the subject that have been transmitted from the terminal device 101, and transmits the data such as the cognitive impairment degree of the subject that has been evaluated by the cognitive impairment degree evaluation unit 40, to the terminal device 101.

In addition, the terminal device 101 having the above-described configuration can be realized by a personal computer, a tablet terminal, a smartphone, and the like that are owned by a doctor, a subject, or a helper of the subject. In addition, the server device 102 can be realized by a high-performance personal computer, a workstation, a general-purpose computer, and the like. In addition, a plurality of terminal devices 101 may be connected to a single server device 102 via a communication network.

In the cerebral dysfunction evaluation apparatus 100a according to the modified example of the present embodiment, the terminal device 101 merely acquires data of a body movement of a subject, and displays an evaluation result of the acquired data. Thus, for example, even if the terminal device 101 is lost, data of a cognitive impairment degree of a subject does not flow out. In addition, since an evaluation result such as a cognitive impairment degree of a subject is stored in the storage device 6 of the server device 102, it becomes easy for concerned persons such as a doctor, a nurse, and a helper to access the evaluation result. In addition, by providing the server device 102, it becomes easy to connect the cerebral dysfunction evaluation apparatus 100a to another medical information/health information management system such as an electronic medical record system, a medication record system, and a health management system.

4.2 Other Modified Examples

In the above-described embodiment of the present invention, and the modified example of the embodiment, the cerebral dysfunction evaluation apparatuses 100 and 100a prompt, via the body movement task selection screen 120 (refer to FIG. 3) on which a plurality of body movement tasks is displayed, a subject to select one body movement task, and prompt the subject to execute the selected one body movement task. In this case, the subject may be prompted to select a plurality of body movement tasks. In such a case, the cognitive impairment degree evaluation unit 40 calculates a plurality of cognitive impairment degrees S according to the respective body movement tasks. The cognitive impairment degrees S may be stored in the storage device 6 in association with the respective body movement tasks. Alternatively, a comprehensive cognitive impairment degree S may be newly calculated by averaging or weighted-averaging the plurality of cognitive impairment degrees S, and the calculation result many be stored in the storage device 6.

In addition, the body movement task selection unit 11 may be excluded from the cerebral dysfunction evaluation apparatuses 100 and 100a, and a subject may be expected to execute only predetermined specific one or more body movement tasks.

In addition, the present invention is not limited to the above-described embodiment, and further include various modified examples. For example, the above embodiment has been described in detail for clearly explaining the present invention, and the present invention is not limited to the one including all the above-described configurations. In addition, part of the configurations of a certain embodiment can be replaced with part of the configurations of another embodiment. Furthermore, part or all of the configurations of a certain embodiment may be added to the configurations of another embodiment.

REFERENCE SIGNS LIST

1, 1a, 1b data processing device
2 body movement presenting device
3 body movement detection sensor
4, 4b operation input device
5, 5b output device
6 storage device
7a, 7b communication device
8 communication network
10 body movement instruction unit
11 body movement task selection unit
12 instruction data generation unit
13 instruction data presenting unit
20 body movement data acquisition unit
21 detection data acquisition unit
22 calibration unit
30 body movement accuracy calculation unit
31 instruction and detection data comparing unit
32 positional accuracy calculation unit
33 time-series accuracy calculation unit
40 cognitive impairment degree evaluation unit
41 cognitive impairment degree calculation unit
42 cognitive impairment degree output unit
60a, 60b data transmission and reception unit
70 cognitive impairment degree output unit
100, 100a cerebral dysfunction evaluation apparatus
101 terminal device
102 server device
110 subject registration information display screen
120 body movement task selection screen
121 check mark
210, 210a reaching task instruction screen
211 black filled circle graphic
212, 222 cross-shaped graphic
213, 225, 228, 231, 241, 251 circular graphic
230 one hand rhythm touch task instruction screen
230a both hand rhythm touch task instruction screen
230b both hand alternate rhythm touch task instruction screen
240 one hand rhythm touch task instruction screen
240a both hand rhythm touch task instruction screen
240b both hand alternate rhythm touch task instruction screen
242 touch instruction graphic
250 metronome-type rhythm touch task instruction screen
252 pendulum
253 fan-shaped graphic
260 one hand finger opening and closing tap task instruction screen 260a both hand finger opening and closing tap task instruction screen
260b both hand alternate finger opening and closing tap task instruction screen
261 fan-shaped graphic
261 opening and closing designation region
262, 263 both end arrow
270 five finger touch task instruction screen
271 touch instruction region
272 touch instruction graphic
280 tracking task instruction screen
281a tracking target graphic
282a trajectory
301, 305 axis
310 straight line
311 lost part
351 broken line
352 solid line

The invention claimed is:

1. A measurement method for cerebral dysfunction evaluation, the method comprising:
    providing a subject with a touch enabled computer, wherein the touch enabled computer includes one or more sensors that measure a position of a touch gesture by a first hand or a second hand of the subject;
    acquiring, using the one or more sensors, a response time and position accuracy for a plurality of prescribed touch gestures performed by the subject, where the response time and the position accuracy for each of the plurality of prescribed touch gestures are acquired by:
        displaying, using the display, a target with a known position on the display,
        detecting, using the one or more sensors, a touch gesture performed in response to the displaying,
        determining, by a processor of the touch enabled computer, the position of the touch gesture detected,
        calculating, by the processor, an elapsed time from the displaying to the detecting as the response time, and
        calculating, by the processor, a difference between the known position and the position of the touch gesture performed in response to the displaying as the position accuracy; and
    generating evaluation data for cerebral dysfunction evaluation based on a correlation between the response time and the position accuracy for the plurality of prescribed touch gestures performed by the subject.

2. The method according to claim 1, wherein a calibration process is performed to account for at least one capability of a visual capability, an auditory capability, and a physical capability that the subject individually has.

3. The method according to claim 1, further comprising:
    calculating, by the processor, a cognitive impairment degree of the subject based on the evaluation data.

4. The method according to claim 1, wherein in the touch gesture performed in response to the displaying is an opening and closing of two fingers of the subject while with the two fingers are kept in touch with the touch enabled computer.

5. The method according to claim 1, wherein in the response time and the position accuracy for each of the plurality of prescribed touch gestures are further acquired by:
    playing, by the touch enabled computer, a sound;
    wherein the response time is calculated based on a time from the playing to the detecting.

6. A non-transitory computer readable storage medium that stores instructions that when executed by a processor of a touch enabled computer, cause the processor to:
    acquire, using one or more sensors of the touch enabled computer, a response time and position accuracy for a plurality of prescribed touch gestures performed by a subject, where the response time and the position accuracy for each of the plurality of prescribed touch gestures are acquired by:
        displaying, using the display, a target with a known position on the display,
        detecting, using the one or more sensors, a touch gesture performed in response to the displaying,
        determining the position of the touch gesture detected,
        calculating an elapsed time from the displaying to the detecting as the response time, and
        calculating a difference between the known position and the position of the touch gesture detected as the position accuracy; and
    generate evaluation data for cerebral dysfunction evaluation based on a correlation between the response time and the position accuracy for the plurality of prescribed touch gestures performed by the subject.

7. The non-transitory computer readable storage medium according to claim 6, wherein the instructions further cause the processor to: the
    perform a calibration process that accounts for at least one capability of a visual capability, an auditory capability, and a physical capability that the subject individually has.

8. The non-transitory computer readable storage medium according to claim 6, wherein the instructions further cause the processor to:
    calculate a cognitive impairment degree of the subject based on the evaluation data.

9. The non-transitory computer readable storage medium according to claim 6, wherein the touch gesture performed in response to the displaying is an opening and closing of two fingers of the subject while with the two fingers are kept in touch with the touch enabled computer.

10. The non-transitory computer readable storage medium according to claim 6, wherein the instructions further cause the processor to:
    playing, using the touch enabled computer, a sound;
    wherein the response time is calculated based on a time from the playing to the detecting.

11. A sensor for evaluation of cerebral dysfunction comprising:
    a memory;
    a display;
    one or more sensors that measure a position of a touch gesture by a first hand or a second hand of a subject;
    a processor communicatively coupled to memory, the display and the one or more sensors, wherein the processor:
    acquires, using the one or more sensors, a response time and position accuracy for a plurality of prescribed touch gestures performed by the subject, where the response time and the position accuracy for each of the plurality of prescribed touch gestures are acquired by:
        displaying, using the display, a target with a known position on the display,
        detecting, using the one or more sensors, a touch gesture performed in response to the displaying,
        determining the position of the touch gesture detected,
        calculating an elapsed time from the displaying to the detecting as the response time, and calculating a difference between the known position and the position of the touch gesture detected as the position accuracy; and generates evaluation data for cerebral dysfunction evaluation based on a correlation between the response time and the position accuracy for the plurality of prescribed touch gestures performed by the subject.

12. The sensor according to claim 11, wherein the processor further:

performs a calibration process to account for at least one capability of a visual capability, an auditory capability, and a physical capability that the subject individually has.

13. The method according to claim 1, further comprising:

storing, in a memory of the touch enabled computer, the evaluation data generated in each of a plurality of time periods; and displaying a relationship between the evaluation data generated in each of the plurality of time periods by rendering the evaluation data in a graph-like form.

14. The method according to claim 13, wherein a horizontal axis of the graph-like form indicates information on measurement date and time, and a vertical axis of the graph-like form indicates information on cognitive impairment degree.

15. The non-transitory computer readable storage medium according to claim 6, wherein the instructions further cause the processor to:

store, the evaluation data generated in each of a plurality of time periods in a memory, and display a relationship between the evaluation data generated in each of the plurality of time periods by rendering the evaluation data in a graph-like form.

16. The non-transitory computer readable storage medium according to claim 15, wherein a horizontal axis of the graph-like form indicates information on measurement date and time, and a vertical axis of the graph-like form indicates information on cognitive impairment degree.

17. The sensor according to claim 11, wherein the processor further:

stores, in the memory, the evaluation data generated in each of a plurality of time periods; and displays a relationship between the evaluation data generated in each of the plurality of time periods by rendering the evaluation data in a graph-like form.

18. The sensor according to claim 17, wherein a horizontal axis of the graph-like form indicates information on measurement date and time, and a vertical axis of the graph-like form indicates information on cognitive impairment degree.

19. The method according to claim 1, wherein the correlation is determined based on a linear analysis.

20. The non-transitory computer readable storage medium according to claim 6, wherein the correlation is determined based on a linear analysis.

* * * * *